US011447522B2

(12) United States Patent
Bodor

(10) Patent No.: US 11,447,522 B2
(45) Date of Patent: Sep. 20, 2022

(54) POTENT SOFT ANTI-INFLAMMATORY CORTICOSTEROID COMPOUNDS AND USES THEREOF

(71) Applicant: Bodor Laboratories, Inc., Miami, FL (US)

(72) Inventor: Nicholas S. Bodor, Bal Harbour, FL (US)

(73) Assignee: BODOR LABORATORIES, INC., Miami, FL (US)

( * ) Notice: Subject to any disclaimer, the term of this patent is extended or adjusted under 35 U.S.C. 154(b) by 125 days.

(21) Appl. No.: 16/620,870

(22) PCT Filed: Jun. 13, 2018

(86) PCT No.: PCT/US2018/037366
§ 371 (c)(1),
(2) Date: Dec. 10, 2019

(87) PCT Pub. No.: WO2018/232007
PCT Pub. Date: Dec. 20, 2018

(65) Prior Publication Data
US 2020/0181191 A1 Jun. 11, 2020

Related U.S. Application Data

(60) Provisional application No. 62/562,099, filed on Sep. 22, 2017, provisional application No. 62/559,201, filed on Sep. 15, 2017, provisional application No. 62/518,922, filed on Jun. 13, 2017.

(51) Int. Cl.
*C07J 7/00* (2006.01)
*A61P 27/02* (2006.01)
*A61P 29/00* (2006.01)
*A61K 9/00* (2006.01)

(52) U.S. Cl.
CPC ............. *C07J 7/009* (2013.01); *A61K 9/0014* (2013.01); *A61K 9/0048* (2013.01); *A61P 27/02* (2018.01); *A61P 29/00* (2018.01)

(58) Field of Classification Search
CPC ...................................................... C07J 7/009
See application file for complete search history.

(56) References Cited

U.S. PATENT DOCUMENTS

| 4,710,495 A | 12/1987 | Bodor |
| 4,996,335 A | 2/1991 | Bodor |
| 5,981,517 A * | 11/1999 | Bodor ............... A61P 27/14 552/616 |

FOREIGN PATENT DOCUMENTS

| BE | 889563 C1 | 11/1981 |
| WO | 97/42214 | 11/1997 |
| WO | WO-9742214 A1 * | 11/1997 ............. A61K 31/56 |

OTHER PUBLICATIONS

Bodor, Nicholas, et al. "Potent analogues of etiprednol dicloacetate, a second generation of soft corticosteroids." J. Pharmacy and Pharmacology. (2017), vol. 69, pp. 1745-1753. (Year: 2017).*
International Search Report and Written Opinion of the International Searching Authority dated Sep. 4, 2018, issued in corresponding International Application No. PCT/US2018/037366, 10 pages.
Kurucz, István et al., "Anti-inflammatory effect and soft properties of etiprednol dicloacetate (BNP-166), a new, anti-asthmatic steroid", Pharmazie, vol. 5, pp. 412-416 (2004).
Taylor, Bruce M. et al., "Roles of adhesion molecules ICAM-1 and a4 integrin in antigen-induced changes in microvascular permeability associated with lung inflammation in sensitized brown Norway rats", American Journal of Respiratory Cell and Molecular Biology, vol. 17, No. 6, pp. 757-766 (1997).
Csanadi, A. et al., "Etiprednol dicloacetate, a new soft glucocorticoid drug candidate. Development of chemistry", Pharmazie, vol. 59, pp. 349-359 (2004).
Samir, Ahmed et al., "Identification of esterase involved in the metabolism of two corticosteroid soft drugs", Biochemical Pharmacology, vol. 127, pp. 82-89 (Mar. 2017).
Schneider, Thorsten et al., "Kinetics and quantitation of eosinophil and neutrophil recruitment to allergic lung inflammation in a brown Norway rat model", American Journal of Respiratory Cell and Molecular Biology, vol. 17, pp. 702-712 (1997).
Buchwald, Peter et al., "Soft glucocorticoid design: structural elements and physicochemical parameters determining receptor-binding affinity" Pharmazie, vol. 59, pp. 396-404 (2004).
Bodor, Nicholas, "Designing safer drugs based on the soft drug approach", Trends in Pharmacological Sciences, vol. 3, No. 2, pp. 53-56 (Dec. 1982).
Bodor, Nicholas, "Soft drugs: Principles and methods for the design of safe drugs", Medicinal Research Reviews, vol. 4, No. 4, pp. 449-469 (Oct. 1984).
Bodor, Nicholas, Soft Drugs. In Encyclopedia of Human Biology, Dulbecco R., vol. 7, No. 76, pp. 1-27 (1991).
Bodor, Nicholas et al., "Molecular Size Based Approach to Estimate Partition Properties for Organic Solutes", The Journal of Physical Chemistry B, vol. 101, No. 17, pp. 3404-3412 (1997).
Buchwald, Peter et al., "Octanol-water partition: Searching for predictive models", Current Medicinal Chemistry, vol. 5, No. 5, pp. 353-380 (Nov. 1998).

(Continued)

*Primary Examiner* — John S Kenyon
(74) *Attorney, Agent, or Firm* — Sheppard, Mullin, Richter & Hampton LLP

(57) ABSTRACT

Potent soft corticosteroid pharmaceutical compositions comprising them and method for use as anti-inflammatory agents. Also, a method for softening fluticasone propionate and similar corticosteroids to arrive at potent but safer alternatives. The compound 5-fluoromethyl 17α-dichloroacetoxy-6α,9α-difluoro-11β-hydroxy-16a-methyl-3-oxoandrosta-1,4-diene-17β-carbothioate, which is equally potent to but safer than fluticasone, is among those provided. Another compound of particular interest is 2-hydroxyethyl 17α-dichloroacetoxy-6α,9α-difluoro-11β-hydroxy-16β-methyl-3-oxoandrosta-1,4-diene-17β-carboxylate.

16 Claims, No Drawings

(56) References Cited

OTHER PUBLICATIONS

Zhou, Jiadi et al., "Improved Synthesis of Fluticasone Propionate", Organic Process Research & Development, vol. 18, No. 8, pp. 928-933 (Aug. 2014).

Huang, Tung-Jung et al., "Effect of topical immunomodulators on acute allergic inflammation and bronchial hyperresponsiveness in sensitised rats", European Journal of Pharmacology, vol. 437, No. 3, pp. 187-194 (Feb. 2002).

Barton, Patrick et al., "Structure-activity relationships in the esterase-catalyzed hydrolysis and transferification of esters and lactones", Journal of the Chemical Society Perkin Transactions, vol. 2, pp. 2021-2029 (Sep. 1994).

Kurucz, István et al., "Potency and specificity of the pharmacological action of a new, anti-asthmatic, topically administered soft steroid, etiprednol dicloacetate (BNP-166)", Journal of Pharmacology and Experimental Therapeutics vol. 307, No. 1, pp. 83-92 (Oct. 2003).

* cited by examiner

POTENT SOFT ANTI-INFLAMMATORY CORTICOSTEROID COMPOUNDS AND USES THEREOF

CROSS-REFERENCE TO RELATED APPLICATIONS

This application is the U.S. National Stage of International Patent Application No. PCT/US2018/037366, filed Jun. 13, 2018, which claims benefit from U.S. Provisional Patent Application No. 62/518,922, filed Jun. 13, 2017, U.S. Provisional Patent Application No. 62/559,201, filed Sep. 15, 2017 and U.S. Provisional Patent Application No. 62/562,099, filed Sep. 22, 2017, all of which are hereby expressly incorporated by reference in their entireties and relied upon and assigned to the assignee hereof.

FIELD

Potent soft corticosteroids, pharmaceutical compositions comprising them and methods for use as anti-inflammatory agents. Also, a method for softening fluticasone propionate and similar corticosteroids to arrive at potent but safer alternatives.

BACKGROUND ART

Topical or other local application of potent glucocorticoids can produce severe toxic effects such as Cushingoid features, pituitary-adrenal suppression, skin atrophy, immunosuppression and inhibition of wound healing. Other kinds of toxic responses, including allergies and cataracts, have resulted from long term use of drugs of this type.

Ophthalmic application of glucocorticosteroids presents additional problems. The protective mechanisms built into the eye allow only small amounts of doses applied to the eye to reach the target sites within the eye; generally, over 90 percent of the total dose will find its way into the general circulation. This in turn leads to serious systemic side effects of the type described above. Moreover, there is a more serious and specific side effect when these drugs are used in the eye, which is an increase in intraocular pressure (IOP). Corticosteroid-induced chronic or acute glaucoma has in fact been reported since the early 1960's. Generally, the corticosteroid is needed only topically to control the inflammation. However, the absorbed steroid is responsible for the serious side effects noted above. It is believed that the effect of the corticosteroid on the aqueous outflow pathway and adjacent tissue glycosaminoglycans (GAG's) is important in the development of glucocorticoid-induced ocular hypertension.

There is, therefore, a serious need for potent local anti-inflammatory steroids, which lack systemic activity and consequently do not produce the serious systemic side effects associated with drugs of this class.

'Soft' steroids are compounds having potent anti-inflammatory activity, comparable with conventional steroids, but with minimal systemic activity. These compounds include $\Delta^4$ and $\Delta^{1,4}$ 17α-alkoxy-11β-hydroxy-3-oxoandrostenes optionally bearing various substituents at the 6, 9 and 16-positions and related 11-substituted compounds, which are esters or thioesters of 17β-carboxylic acids. These 17α-ethers are described in Bodor U.S. Pat. No. 4,710,495. Preferred compounds are taught to be the haloalkyl esters of 17α-alkoxy-11β-hydroxyandrost-4-en-3-one-17β-carboxylic acids.

Another series of 'soft' steroids which are described as having potent anti-inflammatory activity with minimal systemic activity are the 17α-carbonates of Bodor U.S. Pat. No. 4,996,335. These compounds include as preferred embodiments, haloalkyl 17α-alkoxycarbonyloxy-11β-hydroxyandrost-4-en-3-one-17β-carboxylates and the corresponding $\Delta^{1,4}$ compounds, optionally bearing 6α- and/or 9α-fluorine and 16α- or 16β-methyl substituents. One of these compounds is chloromethyl 17α-ethoxycarbonyloxy-11β-hydroxyandrosta-1,4-dien-3-one-17β-carboxylate, also known as loteprednol etabonate (LE), approved by the FDA in 1998 and marketed worldwide in five or more products.

During the design and development of the first generation of the 'soft' corticosteroids, more than 120 compounds were synthesized and studied, combining the soft pharmacophore center of 17α-carbonate-17β-chloromethyl esters, with the usual modifications of the corticosteroid structure, such as fluorination at 6α and/or 9α, methylation at 16α and 16β positions and varying the 17β-ester and 17α-carbonate functions. QSAR studies indicated that the known activity enhancer groups were very effective in the soft steroids of this type as well. The relative receptor binding activity (RRBA) values nicely correlated with presence or absence of the fluoro substituents, the molecular volume (calculated by semi-empirical quantum chemical methods) and calculated partition coefficients. Some of the substituted LE derivatives are extremely potent; for example, the 6α,9α-difluoro-16α-methyl loteprednol derivative showed the highest RRBA among all known corticosteroids (2100 on a scale where dexamethasone is 100). However, it was found that in this class, the more potent the new steroid, the less 'soft' it is. In other words, these are more like the currently known potent corticosteroids, not being easily hydrolyzed/deactivated, but subject to oxidative metabolism. Thus, the compounds substituted at the 6- and 9- and 16-positions were subsequently found to not be true 'soft' drugs after all.

Etiprednol dicloacetate (ED; ethyl 17α-dichloroacetoxy-11β-hydroxyandrosta-1,4-diene-3-one-17β-carboxylate) is a second-generation soft corticosteroid designed using retrometabolic principles starting with the inactive metabolite of prednisolone, $\Delta^1$-cortienic acid (1), which is converted to the 17α-dichloroacetate (2) and by esterification to the ED (3). See SCHEME 1 below; also see Bodor U.S. Pat. No. 5,981,517.

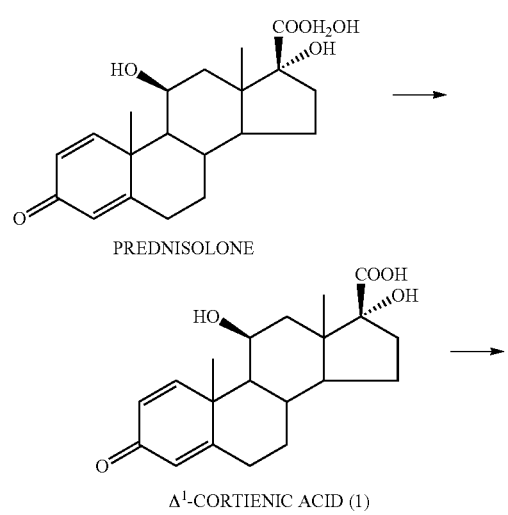

SCHEME 1

PREDNISOLONE $\Delta^1$-CORTIENIC ACID (1)

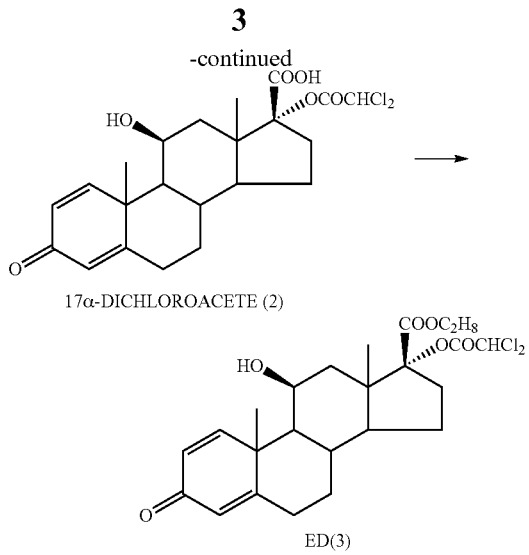

17α-DICHLOROACETE (2)

ED(3)

ED is a unique second generation 'soft' corticosteroid, the first to contain halogen substituents in the 17α-position, which actually serves as the important pharmacophore. It has been shown that the dichloro function is necessary for activity (the monochloro derivative is void of activity, due to the unfavorable position the chlorine is forced into by steric hindrance). The dichloroacetyl functional group is also responsible for the 'soft' nature of ED. Dichloro substituents increase the second order rate constant kcat/kM of enzymatic hydrolysis in acetate esters by a factor of 20, compared to the unsubstituted ester while one chlorine substituent does not cause any change.

Contrary to the first generation of 'soft' corticosteroids based on cortienic acid, represented by Loteprednol Etabonate (LE; 4) which is hydrolytically deactivated by ester cleavage of the 17β-chloromethyl ester, in ED, the hydrolysis does not cleave at the 17β-ester, but primarily cleaves at the 17α-dichloroacetyl function. Nevertheless, the corresponding 17α-OH— metabolites are inactive, thus fulfilling the soft drug requirement.

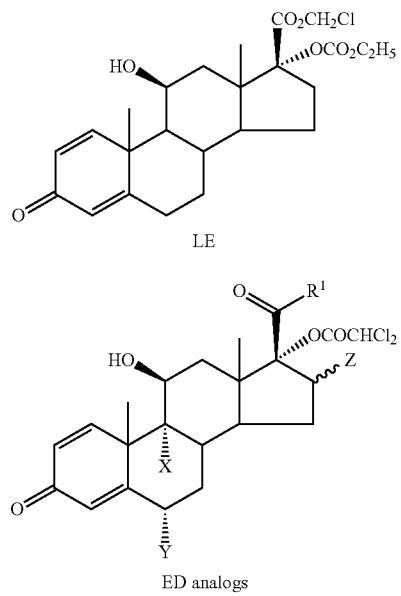

LE (4)

ED analogs (5)

Nevertheless, there remains a serious need in this art for new anti-inflammatory steroids which have potent local anti-inflammatory activity while having minimal or non-existent systemic activity.

SUMMARY

As noted above, the second generation of the soft steroids (etiprednol dicloacetate) based on the $\Delta^1$-cortienic acid, having a 17α-dichloroacetyl function appears to be hydrolyzed primarily not at the 17β-ester, but at the 17α-dichloroacetate. Depending on the animal species, both ester functions can be hydrolyzed, which has a strong influence on the 'soft' nature of these compounds. On the other hand, ED is somewhat more potent than LE (RRBA~200 vs. 160). Surprisingly, the usual potency-enhancing F or Cl at 6α and 9α and 16α-methyl or β-methyl substitution can yield even more potent, but softer corticosteroids, unlike the situation with the first generation LE family of compounds. Accordingly, the synthesis and investigation of the properties of this new selected class of steroids was undertaken and reported here.

In a first major exemplary embodiment of this application, there is provided a soft corticosteroid having high local or topical anti-inflammatory activity and an improved therapeutic index compared to fluticasone propionate, where the compound is represented by the formula (I):

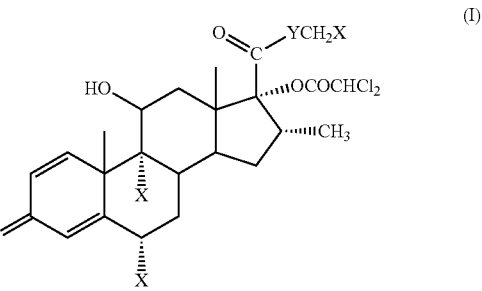

(I)

wherein each X is independently F or Cl, and Y is O or S.

In another exemplary embodiment, the soft corticosteroid of formula (I) is: S-fluoromethyl 17α-dichloroacetoxy-6α,9α-difluoro-11β-hydroxy-16α-methyl-3-oxoandrosta-1,4-diene-17β-carbothioate (fluticasone dicloacetate); S-chloromethyl 17α-dichloroacetoxy-6α,9α-difluoro-11β-hydroxy-16α-methyl-3-oxoandrosta-1,4-diene-17β-carbothioate, fluoromethyl 17α-dichloroacetoxy-6α,9α-difluoro-11 hydroxy-16α-methyl-3-oxoandrosta-1,4-diene-17β-carboxylate, or chloromethyl 17α-dichloroacetoxy-6α,9α-difluoro-11β-hydroxy-16α-methyl-3-oxoandrosta-1,4-diene-17β-carboxylate. Among the compounds of formula (I), the closest analog of fluticasone propionate, i.e. the S-fluoromethyl compound just named, has remarkable activity and still the desired hydrolytic susceptivity and thus is a potent but safer alternative to fluticasone propionate.

In another exemplary embodiment, there is provided a pharmaceutical composition comprising an anti-inflammatory effective amount of a compound having the formula (I):

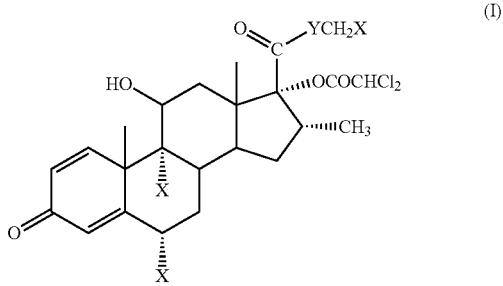

wherein each X is independently selected from the group consisting of F and Cl, and Y is O or S, and a non-toxic pharmaceutically acceptable carrier therefor, suitable for topical or other local application. In further specific embodiments, the compound of formula (I) is S-fluoromethyl 17α-dichloroacetoxy-6α,9α-difluoro-11β-hydroxy-16α-methyl-3-oxoandrosta-1,4-diene-17β-carbothioate, S-chloromethyl 17α-dichloroacetoxy-6α,9α-difluoro-11β-hydroxy-16α-methyl-3-oxoandrosta-1,4-diene-17β-carbothioate; fluoromethyl 17α-dichloroacetoxy-6α,9α-difluoro-11β-hydroxy-16α-methyl-3-oxoandrosta-1,4-diene-17β-carboxylate, or chloromethyl 17α-dichloroacetoxy-6α,9α-difluoro-11β-hydroxy-16α-methyl-3-oxoandrosta-1,4-diene-17β-carboxylate.

In a still further embodiment, there is provided an ophthalmic composition comprising an anti-inflammatory effective amount of a compound of formula (I) above and a non-toxic ophthalmically acceptable carrier therefor. In further specific embodiments, the compound of formula (I) is one of the four specific compounds named above.

Another embodiment herein is a method for alleviating inflammation in or on a warm-blooded animal exhibiting a localized inflammatory response, which comprises locally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Another embodiment herein is a method for alleviating inflammation in or on a warm-blooded animal exhibiting a topical inflammatory response, which comprises topically administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Another embodiment herein is a method for alleviating inflammation in the eye or eyes of a warm-blooded animal exhibiting an ophthalmic inflammatory response, which comprises administering to the eye or eyes of said animal an anti-inflammatory effective amount of a compound of formula (I) as defined above, particularly when the compound is one of the four specific compounds named above, or of an ophthalmic composition as defined above, particularly when the compound of formula (I) is one of the four specific compounds named above.

Another embodiment is a method for alleviating inflammation of the nasal mucosa in a warm-blooded animal exhibiting a nasal inflammatory response, which comprises nasally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Yet another embodiment is a method for alleviating asthma or COPD in the lungs or bronchi of a warm-blooded animal exhibiting an inflammatory response in the lungs or bronchi, which comprises administering to said animal by oral inhalation an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Still another embodiment is a method for alleviating inflammation of the upper or lower intestine in a warm-blooded animal exhibiting an intestinal inflammatory response, which comprises rectally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Another embodiment is a method for alleviating inflammation of the upper or lower intestine in a warm-blooded animal exhibiting an intestinal inflammatory response, which comprises orally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Yet another embodiment is a method for alleviating inflammation in the ear or ears of a warm-blooded animal exhibiting an otic inflammatory response, which comprises administering to the ear or ears of said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Another embodiment is a method for alleviating inflammation in a joint or joints of a warm-blooded animal exhibiting an arthritic inflammatory response, which comprises injecting into said joint or joints an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Still a further embodiment is a method for alleviating inflammation of the skin of a warm-blooded animal exhibiting a dermal inflammatory response, which comprises dermally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

Yet another embodiment herein is a method for alleviating inflammation of the mouth, gums or throat of a warm-blooded animal exhibiting an oral, gingival or throat inflammatory response, which comprises orally administering to said animal an anti-inflammatory effective amount of a compound of formula (I) as defined above, particularly when the compound is one of the four specific compounds named above, or of a pharmaceutical composition as defined above, particularly when the compound of formula (I) is one of the four specific compounds named above.

In a still further embodiment, there is provided a process for softening a 17α-alkylcarbonyloxy-substituted corticosteroid compound of the formula (II):

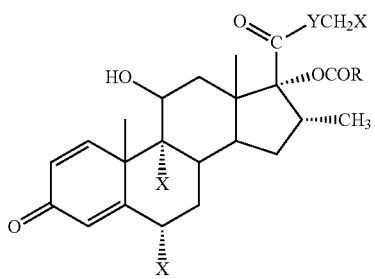

wherein each X is independently F or Cl, Y is O or S and R is $C_1$-$C_3$ alkyl, said compound of formula (II) having local or topical as well as systemic corticosteroid activity, said process comprising synthesizing the corresponding corticosteroid compound wherein the 17α-OCOR group in formula (II) is replaced by a 17α-dichloroacetoxy (17α-OCOCHCl$_2$) group, to provide the resultant soft corticosteroid compound of formula (I):

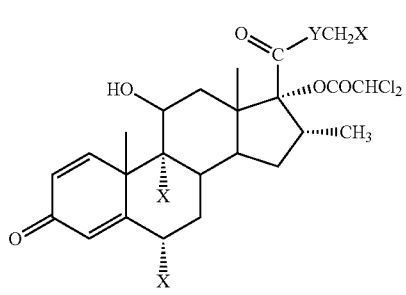

wherein X and Y are as defined with formula (II) above, said compound of formula (I) having substantially equivalent local or topical corticosteroid activity as compared to the corresponding compound of formula (II) but having substantially decreased systemic corticosteroid activity compared to the corresponding compound of formula (II). In specific embodiments of this process, the resultant soft corticosteroid compound of formula (I) is S-fluoromethyl 17α-dichloroacetoxy-6α,9α-difluoro-11β-hydroxy-16α-methyl-3-oxoandrosta-1,4-diene-17β-carbothioate, S-chloromethyl 17α-dichloroacetoxy-6α,9α-difluoro-11β-hydroxy-16α-methyl-3-oxoandrosta-1,4-diene-17β-carbothioate, fluoromethyl 17α-dichloroacetoxy-6α,9α-difluoro-11β-hydroxy-16α-methyl-3-oxoandrosta-1,4-diene-17β-carboxylate, or chloromethyl 17α-dichloroacetoxy-6α,9α-difluoro-11β-hydroxy-16α-methyl-3-oxoandrosta-1,4-diene-17β-carboxylate.

In a second major exemplary embodiment of this application, there is provided a soft corticosteroid having high local or topical anti-inflammatory activity and an improved therapeutic index compared to the corresponding 17α-alkoxycarbonyl (—OCOR) ester, where the compound is represented by the formula (III):

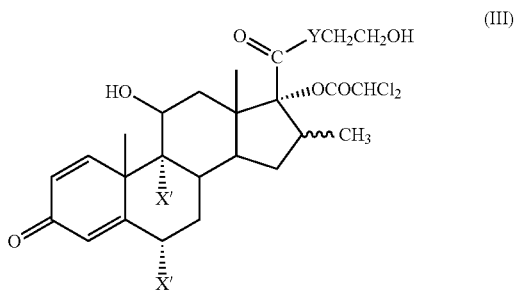

wherein each X' is independently H, F or Cl provided that at least one X' is F or Cl, Y is O or S and the wavy line indicates the α- or β-configuration.

In another exemplary embodiment, the soft corticosteroid of formula (III) is: 2-hydroxyethyl 17α-dichloroacetoxy-6α,9α-difluoro-11β-hydroxy-16β-methyl-3-oxoandrosta-1,4-diene-17β-carboxylate or 2-hydroxyethyl 17α-dichloroacetoxy-9α-fluoro-11β-hydroxy-16β-methyl-3-oxoandrosta-1,4-diene-17β-carboxylate. The compounds of formula (III) have remarkable activity and still the desired hydrolytic susceptivity and are potent but safer alternatives to the corresponding 17α-alkoxycarbonyl (—OCOR) esters.

In another exemplary embodiment, there is provided a pharmaceutical composition comprising an anti-inflammatory effective amount of a compound having the formula (III):

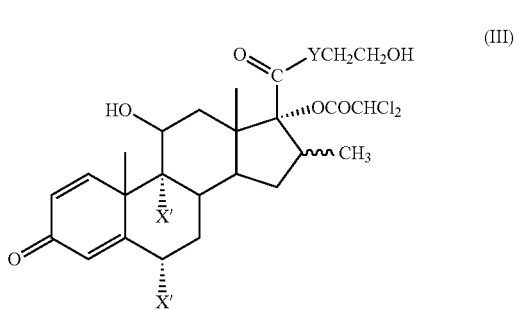

wherein each X' is independently selected from the group consisting of H, F and Cl provided that at least one X' is F or Cl, Y is O or S and the wavy line indicates the α- or β-configuration, and a non-toxic pharmaceutically acceptable carrier therefor, suitable for topical or other local application. In further specific embodiments, the compound of formula (III) is 2-hydroxyethyl 17α-dichloroacetoxy-6α,9α-difluoro-11β-hydroxy-16β-methyl-3-oxoandrosta-1,4-diene-17β-carboxylate or 2-hydroxyethyl 17α-dichloroacetoxy-9α-fluoro-11β-hydroxy-16β-methyl-3-oxoandrosta-1,4-diene-17β-carboxylate.

In a still further embodiment, there is provided an ophthalmic composition comprising an anti-inflammatory effective amount of a compound of formula (III) above and a non-toxic ophthalmically acceptable carrier therefor. In further specific embodiments, the compound of formula (III) is one of the two specific compounds named above.

Another embodiment herein is a method for alleviating inflammation in or on a warm-blooded animal exhibiting a localized inflammatory response, which comprises locally administering to said animal an anti-inflammatory effective amount of a compound of formula (III) as defined above, particularly when the compound is one of the two specific compounds of formula (III) named above, or of a pharmaceutical composition as defined above, particularly when the compound of formula (III) is one of the two specific compounds named above.

Another embodiment herein is a method for alleviating inflammation in or on a warm-blooded animal exhibiting a topical inflammatory response, which comprises topically administering to said animal an anti-inflammatory effective amount of a compound of formula (III) as defined above, particularly when the compound is one of the two specific compounds of formula (III) named above, or of a pharmaceutical composition as defined above, particularly when the compound of formula (III) is one of the two specific compounds named above.

Another embodiment herein is a method for alleviating inflammation in the eye or eyes of a warm-blooded animal exhibiting an ophthalmic inflammatory response, which comprises administering to the eye or eyes of said animal an anti-inflammatory effective amount of a compound of formula (III) as defined above, particularly when the compound of formula (III) is one of the two specific compounds of formula (III) named above, or of an ophthalmic composition as defined above, particularly when the compound of formula (III) is one of the two specific compounds named above.

Another embodiment is a method for alleviating inflammation of the nasal mucosa in a warm-blooded animal exhibiting a nasal inflammatory response, which comprises nasally administering to said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Yet another embodiment is a method for alleviating asthma or COPD in the lungs or bronchi of a warm-blooded animal exhibiting an inflammatory response in the lungs or bronchi, which comprises administering to said animal by oral inhalation an anti-inflammatory effective amount of a compound of formula (III) as defined above, particularly when the compound of formula (III) is one of the two specific compounds of formula (III) named above, or of a pharmaceutical composition as defined above, particularly when the compound of formula (III) is one of the two specific compounds named above.

Still another embodiment is a method for alleviating inflammation of the upper or lower intestine in a warm-blooded animal exhibiting an intestinal inflammatory response, which comprises rectally administering to said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Another embodiment is a method for alleviating inflammation of the upper or lower intestine in a warm-blooded animal exhibiting an intestinal inflammatory response, which comprises orally administering to said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Yet another embodiment is a method for alleviating inflammation in the ear or ears of a warm-blooded animal exhibiting an otic inflammatory response, which comprises administering to the ear or ears of said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Another embodiment is a method for alleviating inflammation in a joint or joints of a warm-blooded animal exhibiting an arthritic inflammatory response, which comprises injecting into said joint or joints an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Still a further embodiment is a method for alleviating inflammation of the skin of a warm-blooded animal exhibiting a dermal inflammatory response, which comprises dermally administering to said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

Yet another embodiment herein is a method for alleviating inflammation of the mouth, gums or throat of a warm-blooded animal exhibiting an oral, gingival or throat inflammatory response, which comprises orally administering to said animal an anti-inflammatory effective amount of a compound of formula (III) as defined above, particularly when the compound of formula (III) is one of the two specific compounds named above, or of a pharmaceutical composition as defined above, particularly when the compound of formula (III) is one of the two specific compounds named above.

In a still further embodiment, there is provided a process for softening a 17α-alkylcarbonyloxy-substituted corticosteroid compound of the formula (IV):

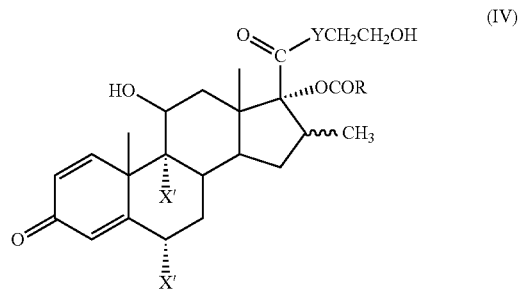

wherein each X' is independently H, F or Cl provided that at least one X' is F or Cl, Y is O or S, R is $C_1$-$C_3$ alkyl and the wavy line indicates the α- or β-configuration, said compound of formula (IV) having local or topical as well as systemic corticosteroid activity, said process comprising synthesizing the corresponding corticosteroid compound wherein the 17α-OCOR group in formula (IV) is replaced by a 17α-dichloroacetoxy (17α-OCOCHCl$_2$) group, to provide the resultant soft corticosteroid compound of formula (III):

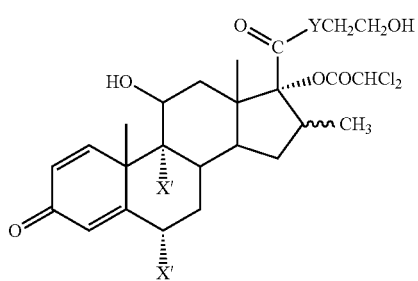

wherein X', Y and the wavy line are as defined with formula (IV) above, said compound of formula (III) having substantially equivalent local or topical corticosteroid activity as compared to the corresponding compound of formula (IV) but having substantially decreased systemic corticosteroid activity compared to the corresponding compound of formula (IV). In specific embodiments of this process, the resultant soft corticosteroid compound of formula (III) is 2-hydroxyethyl 17α-dichloroacetoxy-6α,9α-difluoro-11β-hydroxy-16β-methyl-3-oxoandrosta-1,4-diene-17β-carboxylate, or 2-hydroxyethyl 17α-dichloroacetoxy-9α-fluoro-11β-hydroxy-16β-methyl-3-oxoandrosta-1,4-diene-17β-carboxylate.

In a still further embodiment, there is provided a use of a compound having the formula (I):

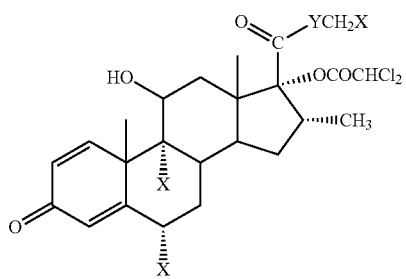

wherein each X is independently F or Cl, and Y is O or S, in the preparation of a pharmaceutical composition suitable for topical or other local application, the pharmaceutical composition comprising an anti-inflammatory effective amount of the compound and a non-toxic pharmaceutically acceptable carrier therefor.

In yet another exemplary embodiment, there is provided a use of a compound having the formula (I):

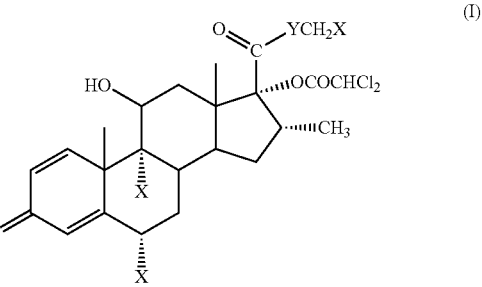

wherein each X is independently F or Cl, and Y is O or S, in the preparation of an ophthalmic composition comprising an anti-inflammatory effective amount of the compound and a non-toxic ophthalmically acceptable carrier therefor.

In a further exemplary embodiment, there is provided a pharmaceutical composition suitable for topical or other local application, the pharmaceutical composition comprising an anti-inflammatory effective amount of a compound having the formula (I):

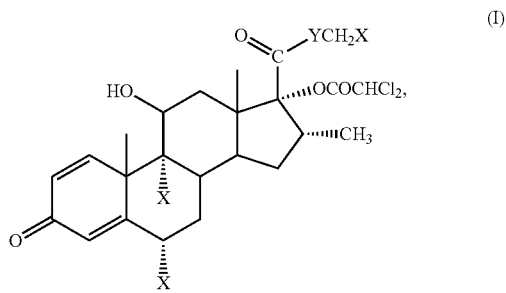

wherein each X is independently F or Cl, and Y is O or S, and a non-toxic pharmaceutically acceptable carrier therefor, for use in alleviating inflammation in or on a warm-blooded animal exhibiting an inflammatory response, wherein the inflammatory response is localized or topical.

In another exemplary embodiment, there is provided an ophthalmic composition comprising an anti-inflammatory effective amount of a compound having the formula (I):

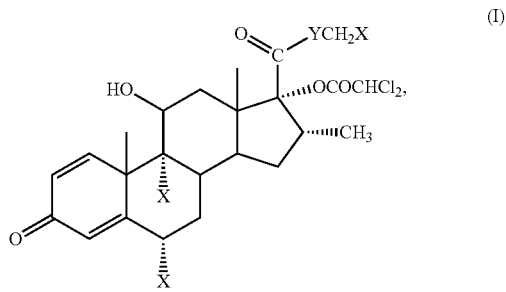

wherein each X is independently F or Cl, and Y is O or S, and a non-toxic ophthalmically acceptable carrier therefor, for use in alleviating inflammation in the eye or eyes of a warm-blooded animal exhibiting an ophthalmic inflammatory response.

In yet another exemplary embodiment, there is provided the use of a 17α-alkylcarbonyloxy-substituted corticosteroid compound of the formula (IV):

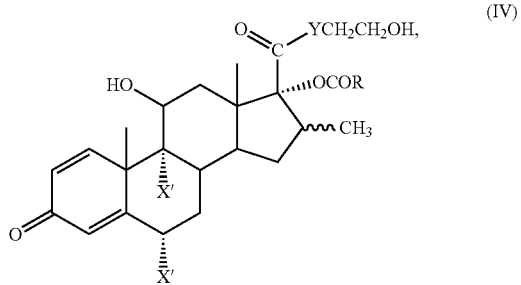

wherein each X' is independently H, F or Cl provided that at least one X' is F or Cl, Y is O or S, R is C1-C3 alkyl and the wavy line indicates the α- or β-configuration, said compound of formula (IV) having local or topical as well as systemic corticosteroid activity, to produce a soft corticosteroid compound of formula (III) by replacing the 17α-OCOR group in formula (IV) with a 17α-dichloroacetoxy (17α-OCOCHCl2) group:

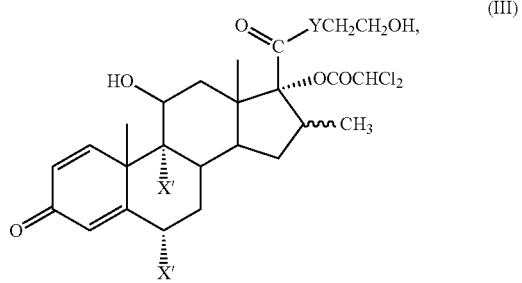

wherein each X' and Y are as defined with formula (IV) above, said compound of formula (III) having substantially equivalent local or topical corticosteroid activity as compared to the corresponding compound of formula (IV) but having substantially decreased systemic corticosteroid activity as compared to the corresponding compound of formula (IV).

In another exemplary embodiment, there is provided the use of compound having the formula (III):

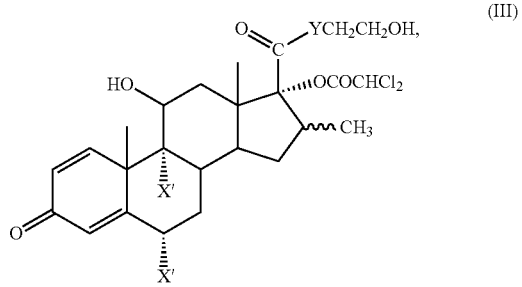

wherein each X' is independently H, F or Cl provided that at least one X' is F or Cl, Y is O or S and the wavy line indicates the α- or β-configuration, in the preparation of a pharmaceutical composition suitable for topical or other local application, the pharmaceutical composition comprising an anti-inflammatory effective amount of the compound and a non-toxic pharmaceutically acceptable carrier therefor.

In yet another exemplary embodiment, there is provided the use of compound having the formula (III):

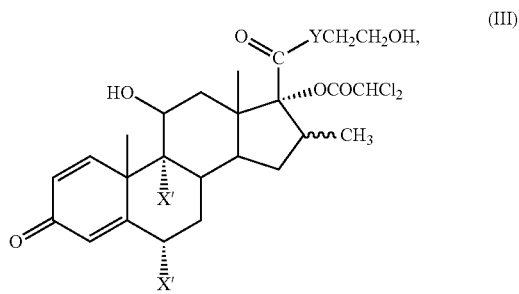

wherein each X' is independently H, F or Cl provided that at least one X' is F or Cl, Y is O or S and the wavy line indicates the α- or β-configuration, in the preparation of an ophthalmic composition comprising an anti-inflammatory effective amount of the compound and a non-toxic ophthalmically acceptable carrier therefor.

In another exemplary embodiment, there is provided a pharmaceutical composition suitable for topical or other local application, the pharmaceutical composition comprising an anti-inflammatory effective amount of a compound having the formula (III):

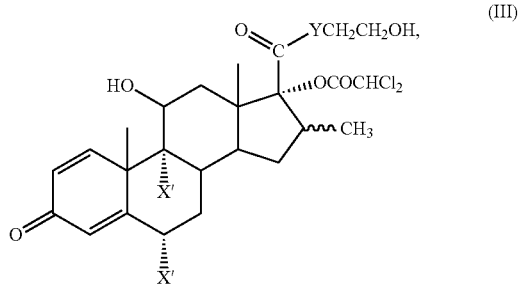

wherein each X' is independently H, F or Cl provided that at least one X' is F or Cl, Y is O or S and the wavy line indicates the α- or β-configuration, and a non-toxic pharmaceutically acceptable carrier therefor, for use in alleviating inflammation in or on a warm-blooded animal exhibiting an inflammatory response, wherein the inflammatory response is localized or topical.

In yet another exemplary embodiment, there is provided an ophthalmic composition comprising an anti-inflammatory effective amount of a compound having the formula (III):

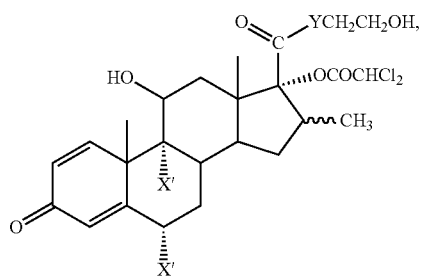

wherein each X' is independently H, F or Cl provided that at least one X' is F or Cl, Y is O or S and the wavy line indicates the α- or β-configuration, and a non-toxic ophthalmically acceptable carrier therefor, for use in alleviating inflammation in the eye or eyes of a warm-blooded animal exhibiting an ophthalmic inflammatory response.

DETAILED DESCRIPTION

The expression 'softening' as used herein means decreasing the systemic corticosteroid activity/toxicity (or side-effects) of an anti-inflammatory corticosteroid by replacing an oxidatively metabolizable structural group in said corticosteroid compound [e.g. as in (II)] with a readily hydrolyzable structural group while maintaining high local/topical corticosteroid activity. In particular, the expression 'softening' means synthesizing a corticosteroid compound [(I) or (III) above] which retains potency-increasing substitution at the 6α, 9α and 16α-positions of the compound (II) or (IV) while replacing the 17α-OCOR group with a 17α-dichloroacetoxy (17α-OCOCHCl$_2$) group to provide the corresponding (I) or (III), respectively.

The synthesis of ED (3) is illustrated in SCHEME 1 above. The ED analogs represented by the general formula 5 were synthesized using a process similar to that shown for the compound of formula 3, but replacing Δ$^1$-cortienic acid with the fluorinated analogs 6 and 7 depicted below.

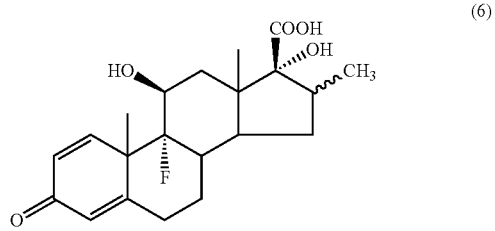

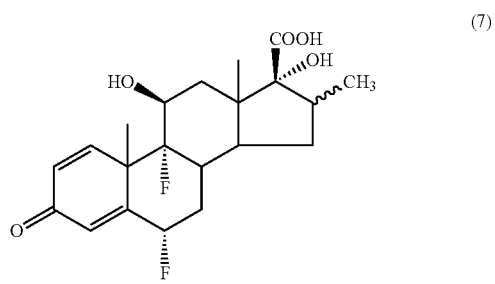

The cortienic acids 6 and 7 were converted to the corresponding 17α-dichloroacetyl esters, which were the starting materials for the various 17β-esters 8-15 listed in following Table 1 and included in the working Examples that follow herewith.

Finally, the commercially available 6α,9α-difluoro-16α-methyl prednisolone (18), the precursor of fluticasone propionate (FLU), one of the most used and highly potent corticosteroids, was oxidized to the corresponding cortienic acid derivative 19, and as needed, 19 was converted to the thiocortienic acid 23. Dichloroacetylation of 19 and 23 to 20 and 24 respectively, and subsequent esterification of the 17β-carboxy function led to the target halo (Cl or F) 16α-methyl esters 21, 22, 25 and 26, as illustrated in SCHEME 2 below.

SCHEME 2

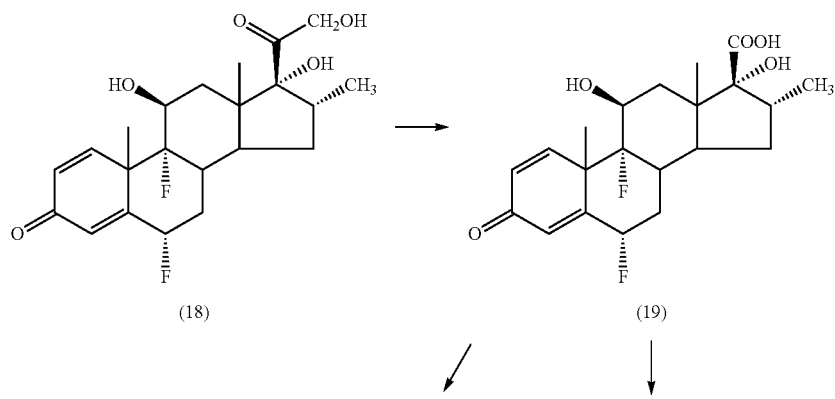

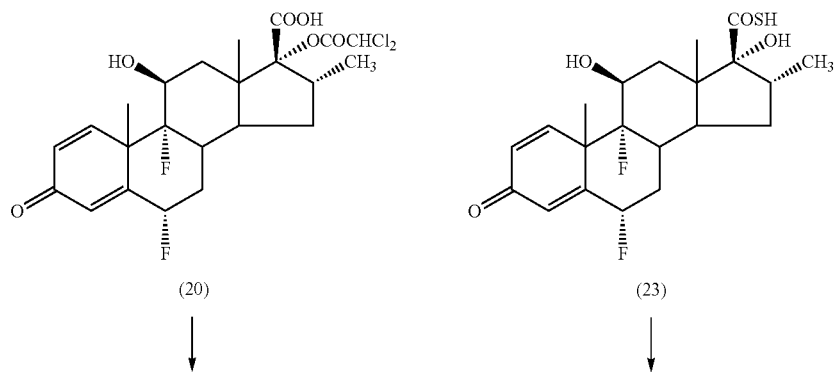
(20)
(23)
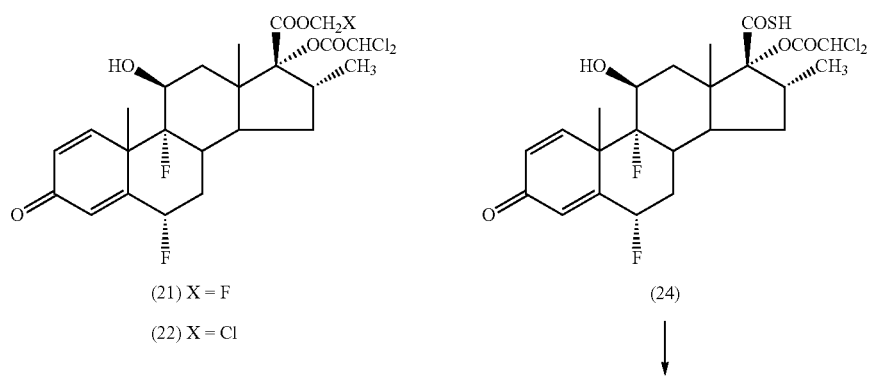
(21) X = F
(22) X = Cl
(24)
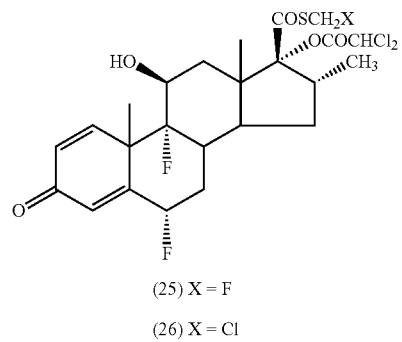
(25) X = F
(26) X = Cl Compound 25 is a soft analog of fluticasone propionate, where the 17α-propionyl function is now replaced by the hydrolytically more labile dichloroacetyl function. Compound 25 or some of the other structural analogs are surprisingly superior to fluticasone in terms of high activity but with improved safety, and thus an improved therapeutic index.

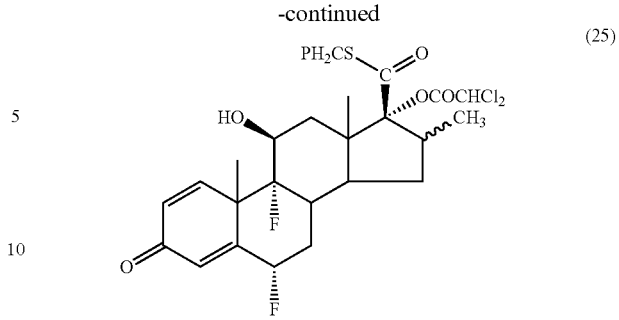

(25)

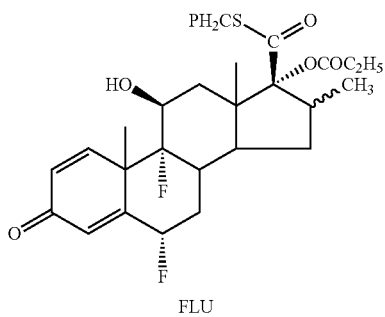

FLU

Etiprednol dicloacetate and its analogs significantly inhibited the liberation of IL-1β from the human monocyte cell line THP-1. The in vitro anti-inflammatory effect of ED and its analogs was assessed using LPS-induced TNF α-release under various conditions (diluted or undiluted whole human blood, preincubation with sera) to determine the intrinsic anti-inflammatory activity and systemic biological stability of the various compounds. The results are shown in Table 1.

Two representative analogs of ED were selected for in vivo studies in the widely-used ovalbumin-sensitized and challenged Brown Norway rat model. Allergic challenge in this animal causes extensive inflammation in the lung with characteristic increase in the number of eosinophils and mucus-producing goblet cells, and in the exudate of perivascular edema. In addition, airway hypersensitivity also develops, which is a cardinal feature of asthma. ED was then compared in this model to the selected 9α-fluoro-16β-methyl analog (11). Finally, the fluticasone analog 25 was compared to fluticasone. The results are summarized in Table 2.

TABLE 1

In vitro anti-inflammatory activity ($IC_{50}$ values in nM) of selected 17α-dichloroacetoxy etiprednol analogs represented by structure (5):

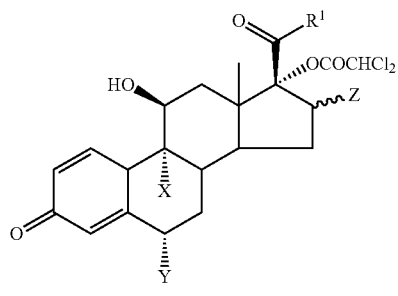

ED analogs (5)

| Compound | X | Y | Z | R' | TNFα* a | TNFα* b | Prolif.** | Stability*** c | Stability*** d |
|---|---|---|---|---|---|---|---|---|---|
| 3 (ED) | H | H | H | $OCH_2CH_3$ | 27 | 103 | 10 | 73 | 2700 |
| 10 | F | H | β-$CH_3$ | $OCH_3$ | 4 ± 3 | 20 ± 10 | <0.01 | 1.7 | 10.2 |
| 11 | F | H | β-$CH_3$ | $OCH_2CH_3$ | 1.7 ± 2 | 7.1 ± 4 | 0.012 | 16 | 18 |
| 12 | F | H | β-$CH_3$ | $OCH_2Cl$ | 20 ± 8 | 35 ± 12 | 0.05 ± 0.12 | — | — |
| 13 | F | H | β-$CH_3$ | $OCH_2CH_2OH$ | 4.6 ± 6.0 | 5.8 ± 5.0 | 0.28 ± 16 | 4.5 | 53.5 |
| 14 | F | F | β-$CH_3$ | $OCH_3$ | 0.8 ± 0.6 | 1.7 ± 0.9 | <0.01 | — | — |
| 15 | F | F | β-$CH_3$ | $OCH_2CH_3$ | 2.0 | 14.0 | <0.01 | — | — |
| 16 | F | F | β-$CH_3$ | $OCH_2Cl$ | 0.4 ± 3 | 5.1 ± 1.7 | 26 ± 26 | — | — |
| 17 | F | F | β-$CH_3$ | $OCH_2CH_2OH$ | <1 | 3.7 ± 2.6 | 0.13 ± 0.020 | 1.9 | 19.2 |

TABLE 1-continued

In vitro anti-inflammatory activity (IC$_{50}$ values in nM) of selected 17α-dichloroacetoxy etiprednol analogs represented by structure (5):

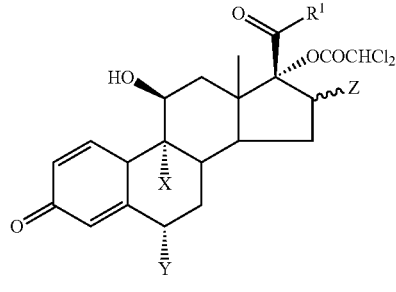

ED analogs (5)

| Compound | X | Y | Z | R' | TNFα* a | TNFα* b | Prolif.** | Stability*** c | Stability*** d |
|---|---|---|---|---|---|---|---|---|---|
| 21 | F | F | α-CH$_3$ | OCH$_2$F | 1.4 | 4.5 | 9 | 1.4 | 25 |
| 22 | F | F | α-CH$_3$ | OCH$_2$Cl | 4.0 | 4.0 | 0.02 | — | — |
| 25 | F | F | α-CH$_3$ | SCH$_2$F | 2.0 | 3.0 | 0.1 | 1 | 87 |
| 26 | F | F | α-CH$_3$ | SCH$_2$Cl | 6.0 | 12.0 | 3 | — | — |

*Inhibition of TNF α-production of LPS-stimulated blood cells. The variations reflect differences in blood of different individuals (3-6 individuals provided blood).
(a) diluted blood 1:5
(b) undiluted
**Inhibition of mitogen-induced proliferation of PBMC.
***Inhibition (IC$_{50}$ in nM) of TNF-α production of LPS-stimulated whole blood cells.
(c) non-preincubated in human plasma
(d) preincubated overnight

TABLE 2

Effect of intratracheally administered (2 hours prior challenge) Etiprednol Dicloacetate (ED), the analog 11, fluticasone (FLU) and its analog 25 on the airway changes of ovalbumin sensitized and challenged Brown Norway rats (N = 10)

| Measured parameter | | Effective Doses* (μg/kg) | ED | 11 | FLU | 25 |
|---|---|---|---|---|---|---|
| AHR** | | ED50 | ≈1.0 | 19.4 | 0.14 | 3.75 |
| | | MSED | ≈1.0 | 20.0 | 0.1 | 10 |
| BALF*** protein | | ED50 | ND | ND | 11.2 | 0.64 |
| | | MSED | | | 10.0 | 100 |
| Eosino philia | BALF*** | ED50 | ≤0.1 | >100 | >100 | 16.1 |
| | | MSED | 0.1 | | 10.0 | 1.0 |
| | Peri-bronchial | ED50 | 0.62 | 10.3 | 10.5 | |
| | | MSED | 0.1 | 12.0 | 1.0 | |
| | Peri-vascular | ED50 | >100 | ND | 45.0 | 83.8 |
| | | MSED | 1.0 | | 10.0 | 1.0 |
| Mucus production | | ED50 | 13.8 | <1 | <1.0 | 7.42 |
| | | | 0.1 | <1 | 1.0 | 100 |
| Edema formation | | ED50 | 2.9 | 93 | 2.8 | <1.0 |
| | | MSED | 0.1 | 0.5 | 1.0 | 1.0 |

*ED50 = 50% effective dose (Prisma); MSED = Minimal statistically significantly effective dose (Mann-Whitney U-test)
**Airways hyperreactivity measured as relative response to maximal acetylcholine dose
*** Broncho-alveolar lavage fluid ND = not determined The inventor and co-workers have previously reported the pronounced anti-inflammatory activity of ED (3) on the TNF-α production on LPS stimulated human blood. The difference in the activity of 3 in undiluted versus diluted (1:5) blood was also noted. The efficacy of ED decreased in parallel with the increase in the amount of serum proteins present and it was demonstrated by LC/MS/MS that this decline in activity coincided with the rate of disappearance of the original compound and the appearance of a proposed major metabolite. At that time the putative degrading enzyme of ED was not known, and it was assumed to be a carboxylesterase. Surprisingly, the main metabolite identified was the 17α-hydroxy derivative, that is, the dichloroacetyl function cleaved easier than the highly hindered 17β-ester.

Recently, the inventor and co-workers have identified the hydrolyzing enzyme to be Paraoxonase 1, which is associated with HDL in human blood. This fact not only explains the effect of the dilution, but also raises the possibility of identifying highly potent corticosteroids having multiple substitutions and yet also having improved therapeutic indexes. As mentioned before, the substituted loteprednol derivatives (6α, 9α, 16-α, β) do not hydrolyze easily, and, thus, are not acceptably 'soft.' Furthermore, fluticasone, an allegedly 'soft' steroid, does not undergo hydrolysis of the 17β-fluoromethyl thio ester, but is instead dependent on the relatively slow P-450 catalyzed metabolism. This application describes studies of ED substituted analogs, including the dichloroacetyl analog of fluticasone (25).

Table 1 shows the in vitro activity results in various conditions. The first column clearly shows the effect of dilution of the blood, with the corresponding IC$_{50}$ up to ten times lower in the undiluted blood. The other important property studied is the effect of pre-incubation before assessing the TNF-α production. This is the indicator of the unexpectedly superior stability of these compounds in the general circulatory system. Previous studies showed that ED (3) loses its activity during incubation (by five-fold in two days, 100-fold in five days). Under the same conditions, the comparably effective dexamethasone and budesonide maintain full activity.

Two of these compounds were selected for further in vivo studies. The 9α-fluoro-16-β-methyl analog (11) of ED and the fluticasone analog (25) were studied in the ovalbumin sensitized Brown Norway rats model. The various parameters measured, including allergen-induced airway hyperreactivity (AHR), allergen induced cellular infiltration (eosinophils in the broncho-alveolar lavage fluid (BALF) and in the lung tissues), goblet cell hyperplasia, increased mucus secretion and allergen-induced perivascular edema formation, are shown in Table 2.

The results clearly demonstrate that the 9α, and the 6α,9α-difluoro and 16-methyl substitution enhance the activity of etiprednol. The most attractive feature, however, is the enhanced soft nature, as reflected by the effect of incubation time with serum/blood on the efficacy. Evidently, the Paraoxonase present hydrolyzes the 17α-dichloroacetyl function, with little slowing down by the substituents, unlike in the LE series. Interestingly, the 9α-F-16β-methyl analog (11) of ED (3) does not represent significant improvement over ED, except in mucus production. On the other hand, the fluticasone analog 25 is overall superior to FLU, primarily in reducing eosinophilia and edema formation.

As illustrated by the results included in Tables 1 and 2, selected substituted analogs of the second-generation soft steroid, ED, unexpectedly/surprisingly possess both high overall local/topical anti-inflammatory activity and significantly improved therapeutic indexes when compared with the hard and 17α-carbonate soft analogs. Particularly, compound 25, the fluticasone analog, promises to be superior to fluticasone, the most potent, but most toxic corticosteroid with the steepest side effects curve.

For the following exemplary embodiments, chemicals were purchased from SIGMA (St. Louis, Mo., USA), unless indicated otherwise. Etiprednol dicloacetate (ethyl 17α-dichloroacetoxy-11β-hydroxyandrosta-1,4-diene-3-one-17β-carboxylate, BNP-166) was synthesized at the Department of Chemistry, Institute for Drug Research, Budapest, Hungary. Urethane, Primazin (2% xylazine), Ketalar (10% ketamine), and the Unopette kit were purchased from Reanal (Budapest, Hungary), Alfasan International BV (AB Woerden, The Netherlands), Parke Davis (London, UK), and BD Biosciences (Franklin Lakes, N.J., USA), respectively.

Example 1: 11β,17α-Dihydroxyandrosta-1,4-diene-3-one-17β-carboxylic Acid (1)

To (70 g, 0.194 mol) of prednisolone in a mixture of tetrahydrofuran (600 ml) and methanol (220 ml) at 30° C. was added a solution of sodium metaperiodate (120 g, 0.561 mol) in warm (50° C.) water (550 ml) over 25 min. The reaction mixture was stirred at room temperature for 2 h. The organic solvents were removed in vacuo. The precipitate was collected by filtration, washed twice with water and without drying dissolved in 0.25 N aqueous sodium hydroxide solution (880 ml). Insoluble impurities were removed by filtration, the clear solution was washed twice with methylene chloride and acidified with 0.5 N hydrochloric acid (550 ml) to pH=1. The precipitate was collected by filtration, washed three times with water and dried at 40° C. until constant weight. Yield: 63.7 g (95%), white crystalline powder. Mp 230° C. (decomp.).

$^1$H NMR (250 MH$_z$, DMSO-d$_6$): δ 0.92 (3H, s, CH$_3$-18), 1.40 (3H, s, CH$_3$-19), 4.36 (1H, ms, H$_\alpha$-11), 5.91 (1H, d, J=10 Hz, H-2).

Example 2: 17α-Dichloroacetoxy-11β-hydroxyandrosta-1,4-diene-3-one-17β-carboxylic Acid (2)

Dichloroacetyl chloride (62.5 ml, 95.8 g; 0.65 mol) in methylene chloride (1500 ml) was slowly added to a stirred solution of potassium bicarbonate (139.5 g, 1.39 mol) and 1 (45.0 g, 0.13 mol) in water (2000 ml) over 2 h. The obtained reaction mixture was acidified with 5 N hydrochloric acid (135 ml) to pH=1-2. The layers were separated and the aqueous layer was extracted with methylene chloride (2×210 ml). The combined organic layers were washed with saturated ammonium chloride solution (2×360 ml). The organic layer was stirred with the solution of potassium bicarbonate (17.1 g, 172 mmol) in water (1000 ml) for 30 min. The process was repeated with the solution of potassium bicarbonate (8.6 g, 86.0 mmol) in water (600 ml). The combined aqueous solutions were washed with methylene chloride (135 ml) and then slowly acidified with 2 N hydrochloric acid to pH=1-2 under stirring. The solution was warmed to 45-50° C. then the precipitated white solids were collected by filtration and washed with water. The obtained white powder was dried at 45° C. in vacuo until constant weight. Yield: 55.4 g (93%), white crystalline powder. Mp 210-214° C.

$^1$H NMR (250 MHz, DMSO-d$_6$): δ1.01 (3H s, CH$_3$-18), 1.41 (cH, s, CH$_3$-19), 5.94 (1H, s, H-4), 6.18 (1H, d, J=10 Hz, H-2), 6.85 (1H, s, CO$_2$—CHCl$_2$), 7.33 (1H, d, H-1).

Example 3: Ethyl 17α-dichloroacetoxy-11β-hydroxyandrosta-1,4-diene-3-one-17β-carboxylate (3) (ED—Etiprednol Dicloacetate)

Method A: By Esterification of 2 with Ethyl Iodide

To a stirred suspension of 2 (50 g, 0.109 mol) and anhydrous potassium carbonate (16.58 g, 0.120 mol) in anhydrous dimethyl formamide (500 ml) was added ethyl iodide (13.1 ml, 25.5 g; 0.164 mol) at room temperature. After stirring for 1.5 h the reaction mixture was diluted with saturated aqueous sodium chloride solution (1000 ml) and stirred for 1 h. The obtained precipitate was collected by filtration and washed with water (3×180 ml). The crude product (53.2 g) was recrystallized from ethyl acetate (400 ml). Yield: 31.9 g (61%), white crystalline powder. Mp 201-202.5° C.

$^1$H NMR (500 MHz, CDCl$_3$): δ 1.06 (3H, s, CH$_3$-18), 1.47 (3H, s, CH$_3$-19), 1.27 (3H, t, CH$_3$CH$_2$O), 4.21 (2H, q, CH$_3$CH$_2$O), 2.97 (1H, m, H$_\beta$-16), 4.53 (1H, m, H$_\alpha$-11), 2.36 (1H, m, H$_\alpha$-6), 2.59 (1H, m, H$_\beta$-6), 5.91 (1H, s, CHCl$_2$), 6.03 (1H, d, H-4), 6.28 (1H, dd, H-2), 7.29 (1H, d, H-1), $^{13}$C NMR (125 MH$_z$, CDCl$_3$): 14.1 (CH$_3$CH$_2$O), 16.9 (C-18), 21.0 (C-19), 61.6 (CH$_3$CH$_2$O), 64.2 (CHCl$_2$), 31.9 (C-6), 69.9 (C-11), 93.4 (C-17), 122.5 (C-4), 127.9 (C-2), 156.0 (C-1), 162.8 (CH$_2$—CHCl$_2$), 169.7 (C-5), 168.3 (CO$_2$—CH$_2$CH$_3$), 186.5 (C-3). MS: EI: [M]$^+$484/486 (3.92/2.6%), m/z 363/365 (8.5/5.7%), m/z 356 (3%), m/z 283 (21%), m/z 265 (34%), m/z 122 (100%), m/z 121 (41%). CI: [M+H]$^+$ 485/487 (93/64%), m/z 122 (100%).

Method B: By Esterification of 2 with Diethyl Sulfate

The procedure described above (Method A) was followed with the difference that diethyl sulfate (21.5 ml, 25.3 g, 0.164 mol) was used instead of ethyl iodide. Yield: 70%.

Example 4: 9α-Fluoro-11β,17α-dihydroxy-16β-methyl-3-oxoandrosta-1,4-diene-17β-carboxylic Acid (6)

Prepared as described for 1 above starting with 9α-fluoroprednisolone. Yield: 89%, white crystalline powder. Mp 258-259° C.

$^1$H NMR (DMSO-d$_6$): δ 1.07 (3H, s, CH$_3$-18), 1.50 (3H, s, CH$_3$-19), 1.14 (3H, d, CH$_3$-16), 2.05 (1H, m, H$_\alpha$-16), 5.19 (1H, m, H$_\alpha$-11), 6.00 (1H, m, H-4), 6.20 (1H, dd, H-2), 7.28

(1H, d, H-1). EI: [M]⁺: 378 (2%), m/z: 358 (18%), 122 (100%), 121 (66%). CI: [M+H]⁺: 379 (100%), m/z: 359 (20%).

Example 5: 6α,9α-Difluoro-11β,17α-dihydroxy-16β-methyl-3-oxoandrosta-1,4-diene-17β-carboxylic Acid (7)

Prepared as described for 1 above starting with 6α,9α-difluoro-prednisolone. Yield: 97%, white crystalline powder. Mp 265-267° C.
¹H NMR (CD₃OD): δ 1.17 (3H, s, CH₃-18), 1.24 (3H, d, CH₃-16), 1.59 (3H, s, CH₃-19), 2.60 (1H, m, H-8), 4.25 (1H, ddd, H$_\alpha$-11), 5.54 (1H, dddd, H$_\beta$-6), 6.29 (1H, m, H-4), 6.32 (1H, dd, H-2), 7.34 (1H, dd, H-1).

Example 6: 17-α-Dichloroacetoxy-9α-fluoro-16β-methyl-11β-hydroxy-3-oxoandrosta-1,4-diene-17β-carboxylic Acid (8)

Dichloroacetyl chloride (3.1 ml, 4.76 g; 32.3 mmol) in dichloromethane (75 ml) was slowly added to a stirred solution of potassium hydrogencarbonate (6.94 g, 69.3 mmol) and 6 (1.75 g, 4.62 mmol) in water (100 ml) over 2 hours. The obtained reaction mixture was acidified with 5 N hydrochloric acid (4.8 ml) to pH=1.2. The layers were separated and the aqueous layer was extracted with dichloromethane (2×10 ml). The combined organic layers were washed with saturated ammonium chloride solution (2×13 ml). The organic layer was stirred with a solution of potassium hydrogencarbonate (0.608 g, 6.07 mmol) in water (35 ml) for 30 minutes. The process was repeated with a solution of potassium hydrogencarbonate (0.306 g, 3.05 mmol) in water (22 ml). The combined aqueous solutions were washed with dichloromethane (10 ml) and then slowly acidified with 2 N hydrochloric acid to pH=1-2 under stirring. The solution was warmed to 45-50° C. then the precipitated white solids were collected by filtration and washed with water. The obtained white powder was dried at 45° C. in vacuo until constant weight. Yield: 1.95 g (86%), white crystalline powder. Mp 193-194° C.
¹H NMR (MeOH-d₄): δ 1.13 (3H, s, CH₃-19), 1.43 (3H, d, CH₃-16), 4.29 (1H, m, H$_\alpha$-11), 6.10 (1H, m, H-4), 6.30 (1H, dd, H-2), 7.40 (1H, d, H-10).

Example 7: 17α-Dichloroacetoxy-6α,9α-difluoro-16β-methyl-11β-hydroxy-3-oxoandrosta-1,4-diene-17β-carboxylic Acid (9)

Prepared as described for 8 above starting with 7. Yield: 78%, white crystalline powder. Mp 186° C.
¹H NMR (CDl₃+3 drops of methanol-d₄): δ 1.07 (3H, s, H-18), 1.40 (3H, d, CH₃-16), 1.51 (3H, s, H-19), 2.17 (1H, m, H$_\alpha$-16), 2.45 (1H, m, H-8), 4.29 (1H, m, H$_\alpha$-11), 5.37 (1H, dddd, H$_\beta$-6), 5.91 (1H, s, CHCl₂), 6.32 (1H, dd, H-2), 6.38 (1H, m, h-4), 7.16 (1H, dd, H-1). ¹³C NMR (CDCl₃+3 drops of methanol-d₄): δ 16.7 (18), 20.0 (CH₃-16), 22.9 (19), 32.6 (8), 33.9 (7), 34.8 (15), 36.1 (12), 43.0 (14), 45.1 (16), 47.3 (13), 48.2 (10), 64.3 (CHCl₂), 71.2 (11), 82.6 (6), 92.7 (17), 99.1 (9), 120.7 (4), 129.7 (2), 151.5 (1), 162.3 (5), 163.4 (OC=O), 169.6 (20), 186.1 (3).

Example 8: Methyl 17α-dichloroacetoxy-9α-fluoro-16β-methyl-11β-hydroxy-3-oxoandrosta-1,4-diene-17β-carboxylate (10)

To a stirred suspension of 8 (0.35 g, 0.8 mmol) and anhydrous potassium carbonate (0.122 g, 0.88 mmol) in anhydrous dimethyl formamide (3.5 ml) methyl iodide (0.17 g, 1.2 mmol) was added at room temperature. After stirring for 1.5 hours the reaction mixture was diluted with saturated aqueous sodium chloride solution (8 ml) and stirred for 90 minutes. The obtained precipitate was collected by filtration and washed with water (3×5 ml). The crude product (0.32 g) was purified by column chromatography on silica gel eluting with dichloromethane-methanol 95:5 then was recrystallized from ethyl acetate/n-hexane. Yield: 90%, off-white crystalline powder. Mp 213-215° C.
¹H NMR (CDCl₃): δ 1.08 (3H, s, CH₃-18), 1.57 (3H, s, CH₃-19), 1.46 (3H, d, CH₃-16), 2.22 (1H, m, H$_\alpha$-16), 4.44 (1H, m, H$_\alpha$-11), 6.14 (1H, m, H-4), 6.35 (1H, dd, H-2), 7.20 (1H, d, H-1), 3.71 (3H, s, CH₃O), 5.91 (1H, s, CHCl₂). ¹³C NMR (CDCl₃): 151.6 (C-1), 130.0 (C-2), 186.3 (C-3), 125.3 (C-4), 166.5 (C-5), 30.9 (C-6), 27.5 (C-7), 33.9 (C-8), 100.0 (C-9), 48.1 (C-10), 72.0 (C-11), 37.3 (C-12), 47.7 (C-13), 43.3 (C-14), 35.0 (C-15), 45.6 (C-16), 20.0 (CH₃-16), 92.8 (C-17), 17.3 (C-18), 23.0 (C-19), 167.8 (C-20), 51.9 (CH₃O), 163.4 (OC=O), 64.3 (CHCl₂).

Example 9: Ethyl 17α-dichloroacetoxy-9α-fluoro-16β-methyl-11β-hydroxy-3-oxoandrosta-1,4-diene-17β-carboxylate (11)

Prepared as described for 10 above starting with 8 and using diethyl sulfate instead of methyl iodide. Yield: ~100%, white crystalline powder. Mp 194-195° C.
¹H NMR (CDCl₃): δ 1.08 (3H, s, CH₃-18), 1.57 (3H, s, CH₃-19), 1.45 (3H, d, CH₃-16), 2.21 (1H, m, H$_\alpha$-16), 4.43 (1H, m, H$_\alpha$-11), 6.13 (1H, m, H-4), 6.34 (1H, dd, H-2), 7.23 (1H, d, H-1), 1.25 (3H, t, CH₃CH₂O), 4.17 (2H, q, CH₃CH₂O), 5.91 (1H, s, CHCl₂). ¹³C NMR (CDCl₃): 152.1 (C-1), 129.8 (C-2), 186.5 (C-3), 125.1 (C-4), 166.0 (C-5), 31.0 (C-6), 27.5 (C-7), 33.9 (C-8), 100.2 (C-9), 48.1 (C-10), 71.9 (C-11), 37.1 (C-12), 47.7 (C-13), 43.3 (C-14), 35.0 (C-15), 45.5 (C-16), 20.0 (CH₃-16), 92.6 (C-17), 17.2 (C-18), 23.0 (C-19), 167.2 (C-20), 14.1 (CH₃CH₂O), 61.0 (CH₃CH₂O), 163.3 OC=O), 64.3 CHCl₂).

Example 10: Chloromethyl 17α-dichloroacetoxy-9α-fluoro-16β-methyl-11β-hydroxy-3-oxoandrosta-1,4-diene-17β-carboxylate (12)

Prepared as described for 11 above starting with 8 and using a 4 molar excess of chloroiodomethane instead of methyl iodide. After stirring for 8.5 hours the reaction mixture was diluted with saturated aqueous sodium chloride solution. The crude product was isolated by extraction with diethyl ether and purified by column chromatography on silica gel eluting ethyl acetate-n-hexane 1:1. The product was then recrystallized from ethyl acetate/n-hexane. Yield: 48%, white crystalline powder. Mp 177-180° C.
¹H NMR (CDCl₃): δ 1.13 (3H, s, CH₃-18), 1.57 (3H, s, CH₃-19), 1.48 (3H, d, CH₃-16), 2.23 (1H, m, H$_\alpha$-16), 4.46 (1H, m, H$_\alpha$-11), 6.15 (1H, m, H-4), 6.36 (1H, dd, H-2), 7.18 (1H, d, H-1), 3.50/5.94 (2H, d, CH₂O), 5.92 (1H, s, CHCl₂). ¹³C NMR (CDCl₃): 151.3 (C-1), 130.1 (C-2), 186.2 (C-3), 125.4 (C-4), 166.3 (C-5), 30.9 (C-6), 27.5 (C-7), 33.9 (C-8), 99.7 (C-9), 48.0 (C-10), 71.9 (C-11), 37.3 (C-12), 48.0 (C-13), 43.5 (C-14), 34.9 (C-15), 45.8 (C-16), 19.9 (CH₃-16), 91.9 (C-17), 16.9 (C-18), 23.0 (C-19), 165.3 (C-20), 68.9 (CH₂O), 163.4 (OC=O), 64.1 (CHCl₂).

Example 11: 2-Hydroxyethyl 17α-dichloroacetoxy-9α-fluoro-16β-methyl-11β-hydroxy-3-oxoandrosta-1,4-diene-17β-carboxylate (13)

Prepared as described for 11 above starting with 8 using a 6 molar excess of 2-bromoethanol instead of methyl iodide and a catalytic amount of potassium iodide. After stirring the reaction mixture for 24 hours and diluting it with water the crude product was isolated by extraction with diethyl ether and was purified by column chromatography on silica gel eluting dichloromethane-methanol 95:5. The product was then crystallized by triturating with n-hexane. Yield: 50%, white crystalline powder. Mp 193° C.

$^1$H NMR (CDCl$_3$): δ 1.11 (3H, s, CH$_3$-18), 1.57 (3H, s, CH$_3$-19), 1.46 (3H, d, CH$_3$-16), 2.23 (1H, m, H$_\alpha$-16), 4.41 (1H, m, H$_\alpha$-11), 6.15 (1H, m, H-4), 6.35 (1H, dd, H-2), 7.21 (1H, d, H-1), 4.28 (2H, m, CH$_2$O), 3.82 (2H, m, CH$_2$OH), 5.93 (1H, s, CHCl$_2$). $^{13}$C NMR (CDCl$_3$): 151.9 (C-1), 129.9 (C-2), 186.5 (C-3), 125.2 (C-4), 166.9 (C-5), 30.9 (C-6), 27.6 (0-7), 33.9 (C-8), 100.0 (C-9), 48.1 (C-10), 72.0 (C-11), 37.0 (C-12), 47.8 (C-13), 43.4 (C-14), 35.0 (C-15), 45.7 (C-16), 20.0 (CH$_3$-16), 92.8 (C-17), 17.2 (C-18), 22.9 (C-19), 167.2 (C-20), 66.5 (CH$_2$O), 60.9 (CH$_2$OH), 163.7 (OC=O), 64.3 (CHCl$_2$).

Example 12: Methyl 6α,9α-difluoro-17α-dichloroacetoxy-16β-methyl-11β-hydroxy-3-oxoandrosta-1,4-diene-17β-carboxylate (14)

Prepared as described for 10 above starting with 9. Yield: 51%, white crystalline powder. Mp 216-217° C.

$^1$H NMR (CDCl$_3$): δ 1.08 (3H, s, H-18), 1.46 (3H, d, CH$_3$-16), 1.55 (3H, s, H-19), 2.50 (1H, m, H-8), 3.72 (3H, s, CH$_3$O), 4.44 (1H, m, H$_\alpha$-11), 5.38 (1H, dddd, H$_\beta$-6), 5.92 (1H, s, CHCl$_2$), 6.38 (1H, dd, H-2), 6.45 (1H, m, H-4), 7.12 (1H, dd, H-1). $^{13}$C NMR (CDCl$_3$): δ 17.2 (18), 20.0 (CH$_3$-16), 23.1 (19), 32.6 (8), 33.9 (7), 34.9 (15), 37.1 (12), 43.0 (14), 45.5 (16), 47.7 (13), 47.9 (10), 51.9 (CH$_3$O), 64.3 (CHCl$_2$), 71.8 (11), 86.3 (6), 92.5 (17), 98.6 (9), 121.3 (4), 130.4 (2), 150.2 (1), 161.0 (5), 163.3 (OC=O), 171.7 (20), 185.4 (3).

Example 13: Ethyl 6α,9α-difluoro-17α-dichloroacetoxy-16β-methyl-11β-hydroxy-3-oxoandrosta-1,4-diene-17β-carboxylate (15)

Prepared as described for 11 above starting with 9. The crude product was recrystallized from ethyl acetate/n-hexane. Yield: 57%, white crystalline powder. Mp 155-156° C.

$^1$H NMR (CDCl$_3$): δ 1.09 (3H, s, H-18), 1.27 (3H, t, CH$_3$CH$_2$O), 1.47 (3H, d, CH$_3$-16), 1.55 (3H, s, H-19), 2.50 (1H, m, H-8), 4.19 (2H, q, CH$_3$CH$_2$O), 4.45 (1H, m, H$_\alpha$-11), 5.91 (1H, s, CHCl$_2$), 5.41 (1H, dddd, H$_\beta$-6), 6.38 (1H, dd, H-2), 6.45 (1H, m, H-4), 7.11 (1H, dd, H-1). $^{13}$C NMR (CDCl$_3$): δ 14.1 (CH$_3$CH$_2$O), 17.2 (18), 20.0 (CH$_3$-16), 23.1 (19), 32.6 (8), 33.9 (7), 34.8 (15), 37.2 (12), 43.0 (14), 45.5 (16), 46.7 (13), 48.0 (10), 61.2 (CH$_3$CH$_2$O), 64.3 (CHCl$_2$), 71.8 (11), 86.5 (6), 92.3 (17), 98.7 (9), 121.3 (4), 130.3 (2), 150.2 (1), 161.0 (5), 163.2 (OC=O), 167.1 (20), 185.4 (3).

Example 14: Chloromethyl 6α,9α-difluoro-17α-dichloroacetoxy-16β-methyl-11β-hydroxy-3-oxoandrosta-1,4-diene-17β-carboxylate (16)

Prepared as described for 12 above starting with 9 using a 4 molar excess of chloroiodomethane instead of methyl iodide. The reaction mixture was stirred for 26.5 hours, then diluted with water. The crude product was isolated by extraction with diethyl ether and purified by column chromatography on silica gel eluting dichloromethane-methanol 95:5. The obtained product was recrystallized from ethyl acetate/n-hexane. Yield: 28%, white crystalline powder. Mp 142-144° C.

$^1$H NMR (CDCl$_3$): δ 1.13 (3H, s, H-18), 1.49 (3H, d, CH$_3$-16), 1.55 (3H, s, H-19), 2.51 (1H, m, H-8), 4.46 (1H, m, H$_\alpha$-11), 5.41 (1H, dddd, H$_\beta$-6), 5.50/5.97 (1H+1H, d, CH$_2$Cl), 5.93 (1H, s, CHCl$_2$), 6.39 (1H, dd, H-2), 6.45 (1H, m, H-4), 7.11 (1H, dd, H-1).

Example 15: 2-Hydroxyethyl 6α,9α-difluoro-17α-dichloroacetoxy-16β-methyl-11β-hydroxy-3-oxoandrosta-1,4-diene-17β-carboxylate (17)

Prepared as described for 13 above starting with 9 using a 6 molar excess of 2-bromoethanol instead of methyl iodide and a catalytic amount of potassium iodide. After stirring of the reaction mixture for 5.5 hours and dilution with water the crude product was isolated by extraction with diethyl ether and purified by column chromatography on silica gel eluting dichloromethane-methanol 95:5. The product was then recrystallized from ethyl acetate/n-hexane. Yield: 45%, white crystalline powder. Mp 205-207° C.

$^1$H NMR (CDCl$_3$+2 drops of methanol-d$_4$): δ 1.05 (3H, s, H-18), 1.44 (3H, d, CH$_3$-16), 1.53 (3H, s, H-19), 2.48 (1H, m, H-8), 3.75 (2H, m, OCH$_2$CH$_2$OH), 3.98/4.44 (1H+1H, m, OCH$_2$CH$_2$OH), 4.31 (1H, m, H$_\alpha$-11), 5.39 (1H, dddd, H$_\beta$-6), 5.93 (1H, s, CHCl$_2$), 6.34 (1H, dd, H-2), 6.40 (1H, m, H-4), 7.18 (1H, dd, H-1).

Example 16: Fluoromethyl 17α-dichloroacetoxy-6α,9α-difluoro-11β-hydroxy-16α-methyl-3-oxoandrosta-1,4-diene-17β-carboxylate (21)

Step 1: Preparation of 17α-dichloroacetoxy-6α,9α-difluoro-11β-hydroxy-16α-methyl-3-oxoandrosta-1,4-diene-17β-carboxylic Acid (20)

11β,17α-Dihydroxy-6α,9α-difluoro-16α-methyl-3-oxoandrosta-1,4-diene-17β-carboxylic acid 19 (2.55 g, 6.5 mmol) was added successively to a solution of KHCO$_3$ (7.0 g) in water (100 ml). To this stirred solution dichloroacetylchloride (3.12 ml, 32.48 mmol) dissolved in dichloromethane (75 ml) was added dropwise at r.t. over 2 h. Stirring was continued 1 h more. Then the reaction mixture was acidified with 1 N HCl and the phases were separated. The organic phase was washed with water, dried and evaporated to give one part of the title product (1.06 g). The watery phase was extracted with ethyl acetate and this extract gave after drying and evaporation another fraction (1.73 g) of the title product. The united product was recrystallized from methanol (25 ml) to give the pure product 20 (2.21 g, 67%). Mp: 206° C. (dec), [α]$_D$: +8.9° (c=0.5, EtOH).

$^1$H NMR (500 MHz, DMSO): δ 0.89 (3H, d, CH$_3$-16), 1.04 (3H, s, H-18), 1.49 (3H, s, H-19), 3.23 (1H, m, H$_\alpha$-16), 4.16 (1H, m, H$_\alpha$-11), 5.47 (1H, d, HOCH$_\alpha$-11), 5.62 (1H, dddd, H$_\beta$-6), 6.11 (1H, d, H-4), 6.28 (1H, dd, H-2), 6.98 (1H, s, CHCl$_2$), 7.24 (1H, d, H-1), 13.02 (1H, COOH).

Anal. Calcd. For C$_{23}$H$_{26}$Cl$_2$F$_2$O$_6$ (507.35): C, 54.44; H, 5.17. Found: C, 53.72; H, 5.02.

Step 2

The carboxylic acid derivative 20 of the previous Step 1 (0.51 g, 1.0 mmol) was dissolved in DMF (7 ml), KHCO$_3$ (0.15 g, 1.5 mmol) was added and after 0.5 h stirring at 0° C. bromofluoromethane gas was introduced by a capillary tube for 1 min. The absorbed amount of gas was ca. 1.7 g.

After 2 h stirring at 0° C. the mixture was left to stand overnight. To reach full conversion another amount of gas (ca. 0.5 g) was then absorbed and stirring was continued 4 h more. The reaction mixture was poured onto ice water and the separated product (0.5 g) was isolated by filtration. The crude title product was recrystallized from methanol (50 ml) using charcoal and the solution was concentrated to a volume of ca. 10 ml. Yield: 0.34 g of 21, mp: 241° C., $[\alpha]_D$: +7.3° (c=0.5, ethyl acetate).

$^1$H NMR (500 MHz, DMSO): δ 0.91 (3H, d, $CH_3$-16), 1.04 (3H, s, H-18), 1.49 (3H, s, H-19), 3.30 (1H, m, $H_{13}$-16), 4.19 (1H, m, $H_\alpha$-11), 5.63 (1H, dddd, $H_\beta$-6), 5.58 (1H, d, HO—$CH_\alpha$-11), 5.75/5.85 (1H+1H, dd, $OCH_2F$), 6.12 (1H, d, H-4), 6.29 (1H, dd, H-2), 7.06 (1H, s, $CHCl_2$), 7.25 (1H, d, H-1). $^{13}$C NMR (125 MHz, DMSO): δ 15.4 ($CH_3$-16), 16.0 (18), 22.6 (19), 64.6 ($CHCl_2$), 69.9 (11), 86.7 (6), 93.7 (17), 94.5 ($OCH_2F$), 99.8 (9), 119.4 (4), 129.1 (2), 151.6 (1), 162.6 (5), 163.3 (O=$CHCl_2$), 166.5 (O=CO), 184.3 (3). Ei-MS: $[M]^+$: 538/540/542 (3/2/1); m/z: 140 (100), 44 (92), 139 (90), 134 (88); Ci-MS: $[M+H]^+$: 539/541/543 (100/71/11).

Example 17: Chloromethyl 17α-dichloroacetoxy-6α,9α-difluoro-11β-hydroxy-16α-methyl-3-oxoandrosta-1,4-diene-17β-carboxylate (22)

17α-Dichloroacetoxy-6α,9α-difluoro-11β-hydroxy-16α-methyl-3-oxoandrosta-1,4-diene-17β-carboxylic acid 20 (1.0 g, 2.0 mmol, Example 5, Step 1) was dissolved in DMF (15.0 ml) and while stirring $KHCO_3$ (0.30 g, 3.0 mmol) was added. After 0.5 h stirring chloroiodomethane (0.58 ml, 8.0 mmol) was added and stirring at r.t. was continued overnight. The mixture was then poured onto ice water and the crude product was isolated by filtration. Recrystallization from ethanol by using charcoal for decolorization gave 0.42 g of the title product 22, mp: 226° C., $[\alpha]_D$: +15.1° (c=0.5, ethyl acetate).

$^1$H NMR (500 MHz, DMSO): δ 0.91 (3H, d, $CH_3$-16), 1.05 (3H, s, H-18), 1.49 (3H, s, H-19), 3.29 (1H, m, $H_\beta$-16), 4.19 (1H, m, $H_\alpha$-11), 5.63 (1H, dddd, $H_\beta$-6), 5.63 (1H, dddd, $H_\beta$-6), 5.63 (1H, d, $HOCH_\alpha$-11), 5.87/5.96 (1H+1H, d, $OCH_2F$), 6.11 (1H, d, H-4), 6.29 (1H, dd, H-2), 7.06 (1H, s, $CHCl_2$), 7.24 (1H, d, H-1). Ei-MS: $[M]^+$: 554/556/558 (3/3/1); m/z: 140 (100), 139 (94), 134 (77); Ci-MS: $[M+H]^+$: 555/557/559 (96/100/36).

Example 18: S-Fluoromethyl 17α-dichloroacetoxy-6α,9α-difluoro-11β-hydroxy-16α-methyl-3-oxoandrosta-1,4-diene-17β-carbothioate (25)

Step 1: Preparation of 17α-Dichloroacetoxy-6α,9α-difluoro-11β-hydroxy-16α-methyl-3-oxoandrosta-1,4-diene-17β-carbothioic Acid (24)

11β,17α-Dihydroxy-6α,9α-difluoro-16α-methyl-3-oxoandrosta-1,4-diene-17β-carbothioic acid 23 (7.6 g, 18.4 mmol) was transformed into the 17α-dichloroacetate derivative according to the procedure as described for 20, Step 1. However, the oily residue that was produced by the evaporation of the last ethyl acetate solution was triturated with diisopropyl ether to give the solid title compound 24 (9.40 g, 97%). This crude substance was purified by recrystallization from chloroform. Yield: 6.67 g (69%), mp: 170° (dec).

Anal. Calcd. For $C_{23}H_{26}Cl_2F_2O_5S$ (523.42): S, 6.13. Found: S 6.19.

Step 2: The carbothioic acid derivative (1.05 g, 2.0 mmol) of the previous Step 1, was dissolved in ethyl acetate (12 ml), water (3.5 ml), triethylamine (0.31 ml, 2.2 mmol) and benzyltributylammonium chloride (90 mg) was added and the stirred heterogenous mixture was cooled to 0° C., then bromofluoromethane gas was introduced by a capillary tube for c. 1 min. The absorbed amount was ca. 1.5 g. Stirring was continued and temperature was let to warm to r.t. during 2 h. TLC investigation (silicagel, eluent: c. hexane-ethyl acetate-acetic acid (5:4:1)) showed complete conversion. The mixture was diluted with ethyl acetate (10 ml), the phases were separated and the organic phase was washed successively with 0.5 N HCl, saturated $NaHCO_3$ solution and brine. The solution was then filtered through a pad of neutral alumina and evaporated to give a solid. Column chromatography on silicagel by using an eluent: N.hexane-ethyl acetate (1:1) gave the title compound 25 (0.80 g, 72%). A sample was recrystallized from ethanol, mp: 267° C., $[\alpha]_D$: +40.0° (c=0.3, ethanol).

$^1$H NMR (500 MHz, pyridine-$d_5$): δ 1.16 (3H, d, $CH_3$-16), 1.44 (3H, s, H-18), 1.73 (3H, s, H-19), 3.61 (1H, m, $H_\beta$-16), 4.68 (1H, m, $H_\alpha$-11), 5.68 (1H, dddd, $H_\beta$-6), 6.07/6.12 (1H+1H, d, $OCH_2F$), 6.60 (1H, dd, H-2), 6.80 (1H, d, H-4), 7.26 (1H, d, H-1), 7.44 (1H, s, $CHCl_2$). Ei-MS: $[M]^+$: 554/556 (2/1); m/z: 139 (100), 333 (89), 140 (73); Ci-MS: $[M+H]^+$: 555/557 (100/69). Anal. Calcd. For $C_{24}H_{27}Cl_2F_3O_5S$ (555.44): S, 5.77. Found: S 5.75.

Example 19: S-Chloromethyl 17α-dichloroacetoxy-6α,9α-difluoro-11β-hydroxy-16α-methyl-3-oxoandrosta-1,4-diene-17β-carbothioate (26)

17α-Dichloroacetoxy-6α,9α-difluoro-11β-hydroxy-16α-methyl-3-oxoandrosta-1,4-diene-17β-carbothioic acid 24 (1.04 g, 2.0 mmol, Step 1) was dissolved in DMF (12 ml) and the solution was cooled to 0° C. $NaHCO_3$ (0.26 g, 3.0 mmol) was added and after 10 min stirring chloroiodomethane (0.22 ml, 3.0 mmol) was added dropwise. The temperature was raised over 1 h to r.t. and stirring was continued for 3 h. The mixture was then poured onto water (240 ml) and the product was extracted with ethyl acetate. The extract was washed with brine, dried and evaporated to dryness. The partially solid residue was purified by column chromatography on silicagel with the eluent chloroform-ethyl acetate (4:1). The main fraction (0.81 g) was triturated with hot methanol and after cooling pure title compound 26 (0.35 g) was collected. Mp: 272° C., $[\alpha]_D$: +59.8° (c=0.5, ethanol).

$^1$H NMR (500 MHz, DMSO): δ 0.94 (3H, d, $CH_3$-16), 1.05 (3H, s, H-18), 1.48 (3H, s, H-19), 3.35 (1H, m, $H_\beta$-16), 4.20 (1H, m, $H_\alpha$-11), 5.19/5.22 (1H+1H, d, $OCH_2Cl$), 5.60 (1H, d, $HOCH_\alpha$-11), 5.63 (1H, dddd, $H_\beta$-6), 6.11 (1H, d, H-4), 6.28 (1H, dd, H-2), 7.06 (1H, s, $CHCl_2$), 7.24 (1H, d, H-1). Ei-MS: $[M]^+$: 577/572 (0.7/0.7); m/z: 333 (100), 139 (62); Ci-MS: $[M+H]^+$: 571/573/575 (94/100/33); m/z: 489/491 (74/56).

Pharmacological Studies

Animals

Male Brown Norway rats, weighing 140 to 170 g at the beginning of the experiments, were purchased from Charles River Hungary LTD (Budapest, Hungary). Upon arrival, the animals were inspected for overt signs of ill health then quarantined for a week before use. They were kept in standard animal cages (five to a cage) on a constant 12-h light/dark cycle. The animals had free access to tap water and standard laboratory chow, also purchased from Charles River. Animals were treated according to the European Communities Council Directive (86/609/EEC), and all the experimental procedures were approved by the Institutional Animal Care Committee (Institute for Drug Research, Budapest, Hungary).

Sensitization, Treatment, and Challenge of Animals

Animals were randomly assigned into various treatment groups (4-5 animals/group), weighed, and numbered. They were sensitized with ovalbumin precipitated on alum (25 µg of ovalbumin+20 mg of $Al(OH)_3$ in 0.5 ml of saline/animal) administered subcutaneously on the back on days 0, 14, and 21. Simultaneously, on each occasion, 0.25 ml ($10^9$ cells/ml) of heat-inactivated *Bordatella pertussis* vaccine was injected intraperitoneally. On the $28^{th}$ day, different doses (0.1, 1.0, 10.0, and 100.0 µg/kg) of the glucocorticoids tested were administered intratracheally 2 h before the challenge. Intratracheal drug application was performed under short-lasting general anesthesia plus muscle relaxation produced by intramuscularly given xylazine (10 mg/kg) and ketamine (10 mg/kg). Animals were kept in supine position, and a special cannula (Vasocan Braunüle) was led through the larynx and was advanced into the midportion of the trachea. Powdered solid substance (10 mg) [vehicle (lactose monohydrate) and active drug] was puffed into the lung by a 5-ml syringe. Control animals were treated with vehicle only. Antigen challenge was carried out by exposing the animals for 1 h to vaporized 1% aqueous solution (saline) of ovalbumin administered via the "nose only inhalation system" (Nose Only Exposure System for Rodents; Technical and Scientific Equipment GmbH, Bad Homburg Germany).

Bronchoalveolar Lavage

Forty-eight hours after challenge, animals were sacrificed by an overdose of urethane, and then bronchoalveolar lavage fluid (BALF) was obtained. After a tracheotomy, a polyethylene catheter was inserted and advanced to the bifurcation of the trachea. The airways were then washed by 3 ml of Hank's balanced salt solution prewarmed to 37° C. Washing was repeated three times with the same volume of buffer, and the washouts were collected into a centrifuge tube containing sodium citrate. Total eosinophil number was counted in the collected BALF after phloxine B staining (Unopette kit).

Measurement of Airway Hyperreactivity Ex Vivo

Tracheae were removed from the animals, and after careful cleaning from the adhesive tissues, they were cut into single rings. Ring preparations were suspended into organ bath chambers containing Krebs' buffer and were maintained at 37° C. with continuous aeration. For the recording of isometric tension changes, rings were placed under 1.0 g of tension, and after an equilibration period of 30 min, cumulative concentration response to acetylcholine was determined. Maximal response of control (sensitized, unchallenged, and nontreated) tracheal rings was obtained at $10^{-3}$ M acetylcholine. The magnitude of this response was defined as 100%. All other contractions were expressed as a percentage and related to the control response. Concentrations of acetylcholine necessary to cause contraction equal to 50% to that of the control were determined for each preparation using linear regression. Two to three rings were investigated from each animal.

Histochemistry

Lung specimens of all lobules from each animal were collected after the bronchoalveolar lavage. Samples were fixed in phosphate-buffered 8% formalin for 2 weeks, and then were routinely processed for histochemistry. Thick sections (5 µm) were cut and mounted on surface-treated slides. Perivascular and peribronchial eosinophilia were determined on modified May-Grünwald-Giemsa-stained sections, by counting all eosinophils within visual fields in all peribronchial and perivascular lung tissue at a magnification of 630×. Perivascular edematous areas were determined on periodic acid-Schiff-stained (PAS) specimens that were counterstained with hematoxylin. Fifty randomly chosen microvessels of each experimental group were digitally exposed (Zeiss Axiocam; Axiovert 200 system) at a magnification of 400×. Measurement of the area of perivascular edema was Performed by Zeiss Axiovision 3.1 software (Carl Zeiss Vision GmbH, Jena, Germany). Extension of the perivascular edema is expressed as a percentage of the area of the respective microvessel. Mucus production and goblet cell hyperplasia were determined on similarly prepared (PAS+hematoxylin) lung tissue sections counting all epithelial cells of each airway segment in the whole preparations at a magnification of 400×. Changes in the number of mucus producing cells are expressed as the ratio of PAS positive goblet cells to all epithelial cells counted in all lobules of tissue sections.

Assay for Cytokines

Commercially available human cytokine ELISA sets were used. TNF-α and GM-CSF sets were purchased from BD Pharmingen, San Diego, Calif., USA) and the IL-1β set was obtained from R&D Systems (Minneapolis, Minn., USA). ELISA was performed according to the manufacturer's protocol. Cell-free supernatants were tested in duplicate. Detection limits were 7.8 pg/ml for TNF-α, 4.7 pg/ml for GM-CSF, and 3.9 pg/ml for IL-1β. Results were expressed as the mean percentage of inhibition. $IC_{50}$ values for test compounds were calculated by linear regression.

IL-1β Production of Stimulated THP.1 Cells

THP.1 cells (human monocytic cell line: American Type Culture Collection. Rockville, Md., USA) were maintained in RPMI-1640 medium, supplemented with 10% FCS, $5 \times 10^{-5}$ M 2-merkapto-ethanol, 2 mM glutamine and antibiotics, and were split in every $3^{rd}$ days. To examine the effect of test compounds $2 \times 10^6$ cells/well (24 well plates in 1 ml/well volume) were stimulated with 1 µg/ml LPS and 25 µg/ml silica for IL-1β production as described previously (Németh et al. 1995). The test compounds were dissolved in RPMI-1640 medium or the medium containing 0.01% DMSO. Two parallel cell cultures per treatment groups were run in three independent experiments. IL-1β levels in cell-free supernatants were determined by ELISA.

TNF-α Production of Lipopolysaccharide-Stimulated Human Blood

Peripheral blood from healthy donors was collected aseptically into sterile heparinized (Vacutainer™) tubes. Whole blood samples from each individual were parallel used both undiluted and after 5-fold dilution with RPMI-1640 medium in every experiment. Blood samples were distributed into 24-well plates and incubated with serial concentrations of the test compounds and 1 µg/ml lipopolysaccharide for 24 h at 37° C. in a $CO_2$ thermostat. Controls were treated with lipopolysaccharide and the vehicle (PBS or 0.01% dimethyl sulfoxide in PBS). After incubation, cell-free supernatants were separated by centrifugation (1000 g for 10 minutes) and stored at −20° C. until determination of the amount of TNF-α. Test compounds were examined in blood samples from five different individuals. Two parallel cultures per treatments were run.

Preincubation of the Experimental Compounds with Serum and Measurement of their Effect on TNF-α Production of Lipopolysaccharides-Stimulated Human Peripheral Blood Mononuclear Cells Mononuclear cells from peripheral blood of healthy donors were isolated on Ficoll-gradient. One million cells in 0.9 ml of RPMI 1640 medium were distributed into 24-well plates and serial concentrations of the test compounds, made in fresh human serum either instantly or 18 h previously, were added (0.05 ml) together with the lipopolysaccharide (0.05 ml; 1 µg/ml final concentration). Preincubation of the compounds with serum was carried out at 37° C. Processing of the cultures was done as described above.

$ED_{50}$ Calculation, Statistical Evaluation $ED_{50}$ values were calculated with GraphPad Prism software (GraphPad Software, Inc., San Diego Calif., USA). Statistical analysis between groups was done with Mann-Whitley U test or with Student's t test; differences between treatments (e.g., etiprednol dicloacetate versus budesonide) was analyzed by two-way ANOVA. All the calculations were done with a Statistica for Windows software version 5.1 (StatSoft Inc., Tulsa, Okla., USA).

Proliferation of Lectin-Stimulated Peripheral Mononuclear Cells

Mononuclear cells from heparinized peripheral blood of healthy donors were isolated on suitable gradient (Optiprep solution, 1.077 g/ml). Serial dilutions of the test compounds (ranging from $2 \times 10^{-6}$ to $2 \times 10^{-8}$ M) were made in 100 µl of medium per well of sterile round-bottomed 96-well microtiter plate. Control wells contained culture medium only. 100 µl of cell suspension ($10^6$ cells/ml), containing concanavalin A (2 µg/ml) was added to each well. Proliferation background control cell suspension did not contain the lectin. All cultures were done in triplicate. Microtiter plates were incubated for 72 h at 37° C., in 5% $CO_2$ containing humidified atmosphere. For the last 18 h of incubation, [$^3$H] thymidine was added to the cells cultures, at 0.1 µCi/well final concentration. At the end of the incubation, cells were harvested to glass microfiber filter (Whatman G/F) and associated radioactivity was determined by liquid scintillation.

Stability of Etiprednol Dicloacetate in the Presence of Human Plasma

Etiprednol dicloacetate (BNP-166) was added to freshly prepared human plasma of healthy donors at a concentration of 5 ng/ml, and were incubated at 37° C. for different intervals. After incubation the amount of the original compound (ethyl-17α-dichloroacetoxy-11β-hydroxyandostra-1,4-diene-3-one-17β-carboxylate), and one of its main metabolite, M-OH (17α,11β-dihydroxyandostra-1,4-diene-3-one-17β-carboxylate) were determined using an HPLC/MS/MS method. In brief: Fluocinolone acetonide served as internal standard (20 ng/ml), samples were extracted with a liquid-liquid extraction on Extrelut® columns, and were separated on a Purospher STAR 30×2 mm (3 µm) reversed phase column at a flow rate of 0.3 ml/min, using a linear gradient with a mobile phase system containing acetonitrile, water and acetic acid. Determination were performed on a triple quadrupole mass spectrometer (Perkin-Elmer SCIEX API 2000) supplied with an electrospray interface operated in the positive ionization mode. The multiple ion monitoring, parent→daughter ion transitions of 485.2→265.2, 375.2→265.2 and 495.2→337.2 were used for the quantification of etiprednol dicloacetate, its M-OH metabolite and for the internal standard respectively. Results are expressed as peak areas normalized to the internal control. Stability of the selected ED analogs (10, 11, 13, 17, 21, 25) were determined as described above for ED (3). Compounds 13, 17, 21 and 25 were particularly stable. It is also noted that compounds 13 and 17 are more potent but softer than the corresponding 17β-C(O)CH$_2$CH$_3$ compounds 11 and 15, respectively. See Table 1 above.

The compounds of formula (I) or (III) can be combined with suitable non-toxic pharmaceutically acceptable carriers to provide pharmaceutical compositions for use in the treatment of topical or other localized inflammation. Obviously, in view of their lack of systemic activity, the compounds of formula (I) and (III) are not intended for treatment of conditions where systemic adrenocortical therapy is indicated, e.g.; adrenocortical insufficiency. As examples of inflammatory conditions which can be treated with pharmaceutical compositions comprising at least one compound of formula (I) or (III) and one or more pharmaceutical carriers; the following can be mentioned: dermatological disorders such as atopic dermatitis, acne, psoriasis or contact dermatitis; allergic states such as bronchial asthma; respiratory diseases such as COM; ophthalmic and optic diseases involving acute and chronic allergic and inflammatory reactions (for example, ophthalmic inflammatory conditions such as blepharitis, conjunctivitis, episcleritis, scleritis, keratitis, anterior uveitis and sympathetic ophthalmia); inflammations of the mouth, gums and/or throat; such as gingivitis or oral aphtha; inflammations of the nasal mucosa, for example, those caused by allergies; inflammations of the upper and lower intestines, such as ulcerative colitis; inflammations associated with arthritis; and anorectal inflammation; pruritus and pain associated with hemorrhoids, proctitis; cryptitis, fissures, postoperative pain and pruritus ani. Such compositions can also be applied locally as a prophylactic measure against the inflammation and tissue rejection which arise in connection with transplants.

Obviously, the choice of carrier(s) and dosage forms will vary with the particular condition for which the composition is to be administered and the route of administration.

Examples of various types of preparations for topical/local administration include ointments, lotions, creams, powders, drops (e.g., eye or ear or nose drops), sprays (e.g., for the nose or throat), suppositories, retention enemas, chewable or suckable tablets or pellets (e.g., for the treatment of aphthous ulcers) and aerosols. Ointments and creams can, for example, be formulated with an aqueous or oily base with the addition of suitable thickening and/or gelling agents and/or glycols. Such base can thus, for example, include water and/or an oil such as liquid paraffin or a vegetable oil such as *arachis* oil or castor oil, or a glycolic solvent such as propylene glycol or 1,3-butanediol. Thickening agents which can be used according to the nature of the base include soft paraffin, aluminum stearate, cetostearyl alcohol, polyethylene glycols, woolfat, hydrogenated lanolin and beeswax and/or glyceryl monostearate and/or non-ionic emulsifying agents.

The solubility of the steroid in the ointment or cream can be enhanced by incorporation of an aromatic alcohol such as benzyl alcohol, phenylethyl alcohol or phenoxyethyl alcohol.

Lotions can be formulated with an aqueous or oily base and will in general also include one or more of the following, namely, emulsifying agents, dispersing agents, suspending agents, thickening agents, solvents, coloring agents and perfumes. Powders can be formed with the aid of any suitable powder base e.g., talc, lactose or starch. Drops can be formulated with an aqueous base also comprising one or more dispersing agents, suspending agents or solubilizing agents, etc. Spray compositions can, for example, be formulated as aerosols with the use of a suitable propellant, e.g., dichlorodifluoromethane or trichlorofluoromethane.

Nebulized or powdered formulations can be prepared for oral inhalation in the treatment of asthma, COPD or the like, as is well-known in the art. Solutions and suspensions can be prepared for oral or rectal administration for use in the treatment of inflammations of the intestines, for example, as described in more detail in the examples hereinafter. Parenteral/injectable formulations can be prepared for direct injection into the joints in the treatment of arthritis in accord with methods well-known to those skilled in the art of parenteral formulations.

The proportion of active ingredient in the compositions will vary with the precise compound used, the type of formulation prepared and the particular condition for which the composition is to be administered. The formulation will generally contain from about 0.0001 to about 5.0% by weight of the compound of formula (I) or (III). Topical preparations will generally contain 0.0001 to 2.5%, preferably 0.01 to 0.5%, and will be administered once daily, or as needed. Also, generally speaking, the compounds of formula (I) or (III) can be incorporated into topical and other local compositions formulated substantially as are such presently available types of compositions containing known glucocorticosteroids, at approximately the same (or in the case of the most potent compounds of the invention, at proportionately lower) dosage levels as compared to known highly active agents such as methyl prednisolone acetate and beclomethasone dipropionate or at considerably lower dosage levels as compared to less active known agents such as hydrocortisone.

Thus, for example, an inhalation formulation suitable for use in the treatment of asthma can be prepared as a metered-dose aerosol unit containing a representative species such as S-fluoromethyl 17α-dichloroacetoxy-6α,9α-difluoro-11β-hydroxy-16α-methyl-3-oxoandrosta-1,4-diene-17β-carbothioate or 2-hydroxyethyl 17α-dichloroacetoxy-6α,9α-difluoro-11β-hydroxy-16β-methyl-3-oxoandrosta-1,4-diene-17β-carboxylate, according to procedures well-known to those skilled in the art of pharmaceutical formulations. Such an aerosol unit may contain a microcrystalline suspension of one of the aforementioned compounds in suitable propellants (e.g., trichlorofluoromethane and dichlorodifluoromethane), with oleic acid or other suitable dispersing agent. Each unit typically contains 1-10 milligrams of the aforesaid active ingredient, approximately 5-50 micrograms of which are released at each actuation.

Another example of a pharmaceutical composition is a foam suitable for treatment of a wide variety of inflammatory anorectal disorders, to be applied anally or perianally, comprising 0.05% to 0.1% of a compound of formula (I) or (III), such as the aforementioned S-fluoromethyl or 2-hydroxyethyl compound, and 1% of a local anesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellants.

Yet another pharmaceutical formulation is a solution or suspension suitable for use as a retention enema, a single dose of which typically contains 20-40 milligrams of a compound of formula (I) or (III) such as the aforementioned S fluoromethyl or 2-hydroxyethyl compound, together with sodium chloride, polysorbate 80 and from 1 to 6 ounces of water (the water being added shortly before use). The suspension can be administered as a retention enema or by continuous drip several times weekly in the treatment of ulcerative colitis.

Other pharmaceutical formulations according to the application are illustrated in the Example which follows.

Formulation Example

| Ointment | | |
|---|---|---|
| Compound of formula (I) or (III), e.g. S-fluoromethyl 17α-dichloroacetoxy-6α,9α-difluoro-11β-hydroxy-16α-methyl-3-oxoandrosta-1,4-diene-17β-carbothioate or 2-hydroxyethyl 17α-dichloroacetoxy-6α,9α-difluoro-11β-hydroxy-16β-methyl-3-oxoandrosta-1,4-diene-17β-carboxylate | 0.2% | w/w |
| Liquid parafin | 10.0% | w/w |
| White soft parafin | 89.8% | w/w |
| Aphthous Ulcer Pellet | | |
| Compound of formula (I) or (III), as above | 0.25 | mg |
| Lactose | 69.90 | mg |
| *Acacia* | 3.00 | mg |
| Magnesium stearate | 0.75 | mg |
| Retention Enema | | |
| Compound of formula (I) or (III), as above | 0.001% | w/v |
| Tween 80 | 0.05% | w/v |
| Ethanol | 0.015% | w/v |
| Propylparaben | 0.02% | w/v |
| Methylparaben | 0.08% | w/v |
| Distilled water | q.s. 100 volumes | |
| Eye Drops | | |
| Compound of formula (I) or (III), as above | 0.1% | w/v |
| Tween 80 | 2.5% | w/v |
| Ethanol | 0.75% | w/v |
| Benzalkonium chloride | 0.02% | w/v |
| Phenyl ethanol | 0.25% | w/v |
| Sodium chloride | 0.60% | w/v |
| Water for injection | q.s. 100 volumes | |

Another example of a suitable nasal spray for treating seasonal or perennial allergic and non-allergic rhinitis is formulated analogously to FLONASE® nasal spray, 50 mcg. Fluticasone propionate, the active component of FLONASE® nasal spray, is replaced in the formulation with a representative compound of formula (I) or (III) herein, preferably S-fluoromethyl 17α-dichloroacetoxy-6α,9α-difluoro-11β-hydroxy-16α-methyl-3-oxoandrosta-1,4-diene-17β-carbothioate or 2-hydroxyethyl 17α-dichlororacetoxy-6α,9α-difluoro-11β-hydroxy-16β-methyl-3-oxoandrosta-1,4-diene-17β-carboxylate. The nasal spray delivers 50 mcg of the microfine compound of formula (I) or (III) by means of a metering, atomizing spray pump. The composition also contains microcrystalline cellulose, sodium carboxymethylcellulose, dextrose, benzalkonium chloride (0.02% w/w), polysorbate 80, phenylethylalcohol (0.25% w/w) and has a pH between 5 and 7. An exemplary dosage is 200 mcg daily (two 50 mcg sprays in each nostril once daily or one 50 mcg spray in each nostril twice daily).

For oral inhalation to treat asthma, for example, the fluticasone propionate present in FLOVENT® HFA 44 mcg oral inhalation aerosol, FLOVENT® HFA 110 mcg oral inhalation aerosol or FLOVENT® HFA 220 mcg oral inhalation aerosol can be replaced with an equivalent quantity of a compound of formula (I) or (III) herein, preferably S-fluoromethyl 17α-dichloroacetoxy-6α,9α-difluoro-11β-hydroxy-16α-methyl-3-oxoandrosta-1,4-diene-17β-carbothioate or 2-hydroxyethyl 17α-dichloroacetoxy-6α,9α-difluoro-11β-hydroxy-16β-methyl-3-oxoandrosta-1,4-diene-17β-carboxylate. In addition to the micronized corticosteroid, each inhaler contains the propellant HFA-134a (1,1,1,2-tetrafluoroethane). In the case of the S-fluoromethyl compound, each activation of the propellant delivers the equivalent of 44, 110 or 220 mcg of the corticosteroid fluticasone propionate.

All US patents and all literature articles identified hereinabove and herebelow are incorporated by reference in their entireties and relied upon.

REFERENCES

Bodor N. Androstene derivatives, U.S. Pat. No. 5,981,517; 1999. Pat. WO 97/42,214.

Kurucz I, Németh K, Mészáros S, Török, K, Nagy Z, Zubovics Z, Horváth K, Bodor N. Anti-inflammatory effect and soft properties of etiprednol dicloacetate (BNP-166), a new, anti-asthmatic steroid. *Pharmazie.* 2004; 5:412-416.

Kurucz I, Tóth S, Németh K, Török K, Csillik-Perczel V, Pataki Á, Salamon C, Nagy Z, Székely J, Horváth K, Bodor N. Potency and specificity of the pharmacological action of a new, anti-asthmatic, topically administered soft steroid, etiprednol dicloacetate (BNP-166). *J. Pharm. & Exp. Ther.* 2003; 307(1):83-92. Also published online Jul. 31, 2003 as DOI:10.1124/jpet.103.053652.

Csanádi Á, Horváth Gy, Szekeres T, Haskó T, Ila L, Ivanics J, Patthy M, Salát J, Seres G, Pallagi I, Tóth G, Szederkényi F, Kónya A, Tegdes A, Bodor N, Zubovics Z. Etiprednol dicloacetate, a new soft glucocorticoid drug candidate. Development of chemistry. *Pharmazie.* 2004; 5:349-359.

Bodor N, Buchwald P. *Retrometabolic Drug Design and Targeting.* 2012; ISBN 978-0-470-94945-0.

Buchwald P, Bodor N. Soft glucocorticoid design: structural elements and physicochemical parameters determining receptor-binding affinity. *Pharmazie.* 2004; 5:396-404.

Barton P, Laws A P, Page M I. Structure-activity relationships in the esterase-catalyzed hydrolysis and transferification of esters and lactones. *J Chem Soc Perkin Trans.* 1994; 2:2021-2029.

Bodor N. Soft steroids having anti-inflammatory activity. U.S. Pat. No. 4,996,335; 1991. Belgium Patent BE 889, 563; C1.C073; 1981.

Bodor N. Designing safer drugs based on the soft drug approach. *Trends Pharmacol.* 1982; 3:53-56.

Bodor N. Soft drugs: principles and methods for the design of safer drugs. *Med Res Rev.* 1984; 3:449-469.

Bodor N. Soft Drugs. In *Encyclopedia of Human Biology*, Dulbecco R ed. 1991; 7(76):1-27.

Bodor N, Buchwald P. Molecular size based approach to estimate partition properties for organic solutes. *J Phys Chem B.* 1997; 101:3404-3412.

Buchwald P, Bodor N. Octanol-water partition: searching for predictive models. *Curr Med Chem.* 1998; 5:353-380.

Zhou J, Jin C, Weike S. Improved Synthesis of Fluticasone Propionate. *Org Process Res Dev.* 2014; 18:928-933; and references cited therein.

Huang T J, Eynott P, Salmon M, Nicklin P L, Chung K F. Effect of topical immunomodulators on acute allergic inflammation and bronchial hyperresponsiveness in sensitised rats. *Eur J Pharmacol.* 2002; 437:187-194.

Schneider T, van Velzen D, Moqbel R, Issekutz A C. Kinetics and quantitation of eosinophil and neutrophil recruitment to allergic lung inflammation in a brown Norway rat model. *Am J Respir Cell Mol Biol.* 1997; 17:702-712.

Taylor B M, Kolbasa K P, Chin J E, Richards I M, Fleming W E, Griffin R L, Fidler S F, Sun F F. Roles of adhesion molecules ICAM-1 and α4 integrin in antigen-induced changes in microvascular permeability associated with lung inflammation in sensitized brown Norway rats. *Am J Respir Cell Mol Biol.* 1997; 17:757-766.

Samir A, Bodor N, Imai T. Identification of esterase involved in the metabolism of two corticosteroid soft drugs. *Biochemical Pharmacology.* 2017; 127:82-89.

What is claimed is:

1. A compound having the formula (I):

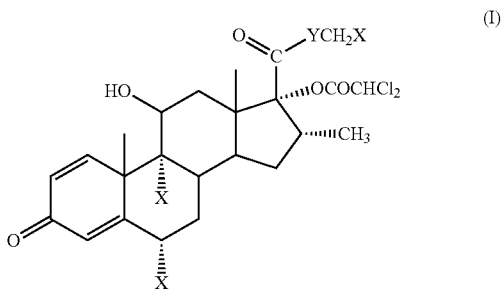

wherein each X is independently F or Cl, and Y is S.

2. The compound of claim 1, selected from the group consisting of S-fluoromethyl 17α-dichloroacetoxy-6α,9α-difluoro-11β-hydroxy-16α-methyl-3-oxoandrosta-1,4-diene-17β-carbothioate, and S-chloromethyl 17α-dichloroacetoxy-6α,9α-difluoro-11β-hydroxy-16α-methyl-3-oxoandrosta-1,4-diene-17β-carbothioate.

3. A pharmaceutical composition comprising an anti-inflammatory effective amount of the compound of claim 1, and a non-toxic pharmaceutically acceptable carrier therefor, suitable for topical or other local application.

4. An ophthalmic composition comprising an anti-inflammatory effective amount of the compound of claim 1, and a non-toxic ophthalmically acceptable carrier therefor.

5. A method for alleviating inflammation in or on a warm-blooded animal exhibiting an inflammatory response, which comprises administering to said animal an anti-inflammatory effective amount of the compound of claim 1 or of a composition comprising an anti-inflammatory effective amount of said compound and a non-toxic pharmaceutically acceptable carrier therefor, suitable for topical or other local application, wherein the administration is local when the inflammatory response is localized or the administration is topical when the inflammatory response is topical.

6. The method according to claim 5, which is:
  (a) A method for alleviating inflammation in the eye or eyes of a warm-blooded animal exhibiting an ophthalmic inflammatory response, which comprises administering to the eye or eyes of said animal an anti-inflammatory effective amount of said compound or composition;
  (b) A method for alleviating inflammation of the nasal mucosa in a warm-blooded animal exhibiting a nasal inflammatory response, which comprises nasally administering to said animal an anti-inflammatory effective amount of said compound or composition;
  (c) A method for alleviating asthma or COPD in a warm-blooded animal exhibiting an inflammatory response in the lungs or bronchi, which comprises administering to said animal by oral inhalation an anti-inflammatory effective amount of said compound or composition;
  (d) A method for alleviating inflammation of the upper or lower intestine in a warm-blooded animal exhibiting an intestinal inflammatory response, which comprises administering to said animal an anti-inflammatory effective amount of said compound or composition, wherein the administration is rectal or oral;

(e) A method for alleviating inflammation in the ear or ears of a warm-blooded animal exhibiting an otic inflammatory response, which comprises administering to the ear or ears of said animal an anti-inflammatory effective amount of said compound or composition;

(f) A method for alleviating inflammation in a joint or joints of a warm-blooded animal exhibiting an arthritic inflammatory response, which comprises injecting into said joint or joints an anti-inflammatory effective amount of said compound or composition;

(g) A method for alleviating inflammation of the skin of a warm-blooded animal exhibiting a dermal inflammatory response, which comprises dermally administering to said animal an anti-inflammatory effective amount of said compound or composition; or (h) A method for alleviating inflammation of the mouth, gums or throat of a warm-blooded animal exhibiting an oral, gingival or throat inflammatory response, which comprises orally administering to said animal an anti-inflammatory effective amount of said compound or composition.

7. A process for softening a 17α-alkylcarbonyloxy-substituted corticosteroid compound of the formula (II)

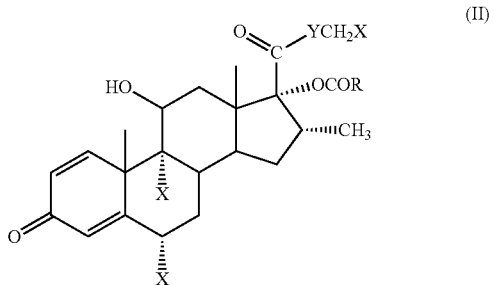

wherein each X is independently F or Cl, Y is S, and R is $C_1$-$C_3$ alkyl, said compound of formula (II) having local or topical as well as systemic corticosteroid activity, said process comprising synthesizing the corresponding corticosteroid compound wherein the 17α-OCOR group in formula (II) is replaced by a 17α-dichloroacetoxy (17α-OCOCHCl$_2$) group, to provide the resultant soft corticosteroid compound of formula (I)

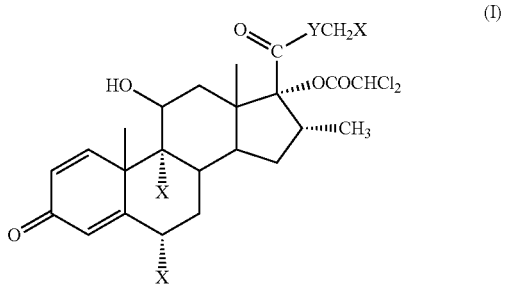

wherein each X and Y are as defined with formula (II) above.

8. The process according to claim 7, wherein the resultant soft corticosteroid compound of formula (I) is selected from the group consisting of S-fluoromethyl 17α-dichloroacetoxy-6α,9α-difluoro-11β-hydroxy-16α-methyl-3-oxoan-drosta-1,4-diene-17β-carbothioate, and S-chloromethyl 17α-dichloroacetoxy-6α,9α-difluoro-11β-hydroxy-16α-methyl-3-oxoandrosta-1,4-diene-17β-carbothioate.

9. A compound having the formula (III):

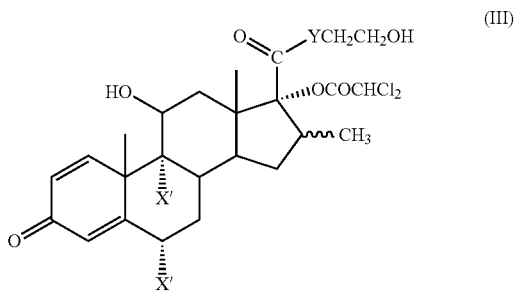

wherein each X' is independently H, F or Cl provided that at least one X' is F or Cl, Y is O or S and the wavy line indicates the α- or β-configuration.

10. The compound of claim 9, selected from the group consisting of 2-hydroxyethyl 17α-dichloroacetoxy-6α,9α-difluoro-11β-hydroxy-16β-methyl-3-oxoandrosta-1,4-diene-17β-carboxylate and 2-hydroxyethyl 17α-dichloroacetoxy-9α-fluoro-11β-hydroxy-16β-methyl-3-oxoandrosta-1,4-diene-17β-carboxylate.

11. A pharmaceutical composition comprising an anti-inflammatory effective amount of the compound of claim 9, and a non-toxic pharmaceutically acceptable carrier therefor, suitable for topical or other local application.

12. An ophthalmic composition comprising an anti-inflammatory effective amount of the compound of claim 9, and a non-toxic ophthalmically acceptable carrier therefor.

13. A method for alleviating inflammation in or on a warm-blooded animal exhibiting an inflammatory response, which comprises administering to said animal an anti-inflammatory effective amount of the compound of claim 9 or of a composition comprising an anti-inflammatory effective amount of said compound and a non-toxic pharmaceutically acceptable carrier therefor, suitable for topical or other local application; wherein the administration is local when the inflammatory response is localized or the administration is topical when the inflammatory response is topical.

14. The method according to claim 13, which is:

(a) A method for alleviating inflammation in the eye or eyes of a warm-blooded animal exhibiting an ophthalmic inflammatory response, which comprises administering to the eye or eyes of said animal an anti-inflammatory effective amount of said compound or composition;

(b) A method for alleviating inflammation of the nasal mucosa in a warm-blooded animal exhibiting a nasal inflammatory response, which comprises nasally administering to said animal an anti-inflammatory effective amount of said compound or composition;

(c) A method for alleviating asthma or COPD in a warm-blooded animal exhibiting an inflammatory response in the lungs or bronchi, which comprises administering to said animal by oral inhalation an anti-inflammatory effective amount of said compound or composition;

(d) A method for alleviating inflammation of the upper or lower intestine in a warm-blooded animal exhibiting an intestinal inflammatory response, which comprises administering to said animal an anti-inflammatory effective amount of said compound or composition, wherein the administration is rectal or oral;
(e) A method for alleviating inflammation in the ear or ears of a warm-blooded animal exhibiting an otic inflammatory response, which comprises administering to the ear or ears of said animal an anti-inflammatory effective amount of said compound or composition;
(f) A method for alleviating inflammation in a joint or joints of a warm-blooded animal exhibiting an arthritic inflammatory response, which comprises injecting into said joint or joints an anti-inflammatory effective amount of said compound or composition;
(g) A method for alleviating inflammation of the skin of a warm-blooded animal exhibiting a dermal inflammatory response, which comprises dermally administering to said animal an anti-inflammatory effective amount of said compound or composition; or
(h) A method for alleviating inflammation of the mouth, gums or throat of a warm-blooded animal exhibiting an oral, gingival or throat inflammatory response, which comprises orally administering to said animal an anti-inflammatory effective amount of said compound or composition.

15. The process according to claim 7, wherein said compound of formula (I) has substantially equivalent local or topical corticosteroid activity as compared to the corresponding compound of formula (II), but has substantially decreased systemic corticosteroid activity as compared to the corresponding compound of formula (II).

16. The process according to claim 7, wherein said compound of formula (I) has an improved therapeutic index compared to the corresponding compound of formula (II).

* * * * *